United States Patent
Yasuda et al.

(10) Patent No.: US 7,085,651 B2
(45) Date of Patent: Aug. 1, 2006

(54) METHOD AND DEVICE FOR ASSEMBLING NUCLEIC ACID BASE SEQUENCES

(75) Inventors: Tomohiro Yasuda, Kokubunji (JP); Tetsuo Nishikawa, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 271 days.

(21) Appl. No.: 10/083,338

(22) Filed: Feb. 27, 2002

(65) Prior Publication Data
US 2003/0104408 A1 Jun. 5, 2003

(30) Foreign Application Priority Data
Nov. 19, 2001 (JP) ............................. 2001-353640

(51) Int. Cl.
G06F 17/11 (2006.01)
G06F 17/50 (2006.01)
G06F 19/00 (2006.01)

(52) U.S. Cl. .......................................... 702/19; 702/20
(58) Field of Classification Search ................. 702/19, 702/20
See application file for complete search history.

(56) References Cited
OTHER PUBLICATIONS

Xiaoqiu Huang and Anup Madan, "CAP3: a DNA Sequence Assembly Program", Genome Research (1999) pp. 868-877.

Zheng Zhang, Scott Schwartz, Lukas Wagner and Webb Miller, "A greedy Algorithm for Aligning DNA Sequences", Journal of Computational Biology, vol. 7, No. 1/2 , 2000, pp. 203-214.

Stephen F. Altshcul, Thomas L. Madden, Alejandro A. Schaffer, Jinghui Zhang, Zheng Zhang, Webb Miller and David J. Lipman, "Gapped BLAST and PSI-BLAST: a New Generation of Protein Database Search Programs", Nucleic Acids Research, 1997, vol. 25, No. 17, pp. 3389-3402.

*Primary Examiner*—Michael Borin
(74) *Attorney, Agent, or Firm*—Reed Smith LLP; Stanley P. Fisher, Esq.; Juan Carlos A. Marquez, Esq.

(57) ABSTRACT

An object of the present invention is to perform the clustering and assembling of nucleic acid base sequences at a high speed. Partial sequences 102 are extracted from each input sequence 101 and entered into a fixed-length partial sequence table 103. In the case where a sequence overlapping with a consensus sequence 104 is searched while making reference to the fixed-length partial sequence table 103 and consequently a partial sequence 102, which exactly matches with a sequence defined by a fixed length window 105 scanning along the consensus sequence, is found to be present, whether the whole input sequence can be assembled or not is determined by comparing the sequences. If it is possible to assemble the sequences, they are assembled into a consensus sequence and also joined into the same cluster. The clustering and assembling are performed by repeatedly processing this procedure based on greedy method until no unprocessed input nucleic acid base sequence is left.

14 Claims, 16 Drawing Sheets

FIG.3
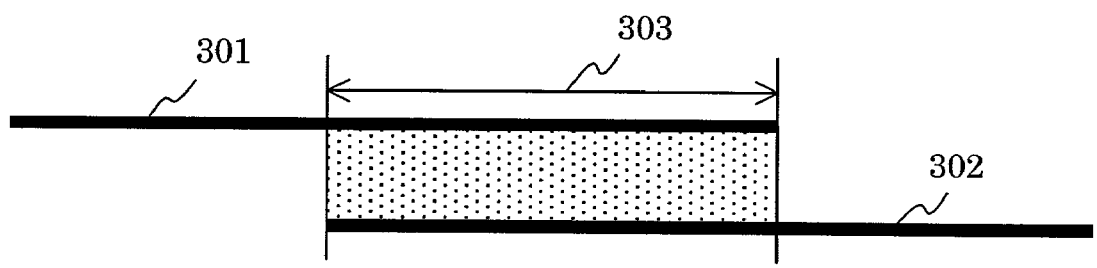
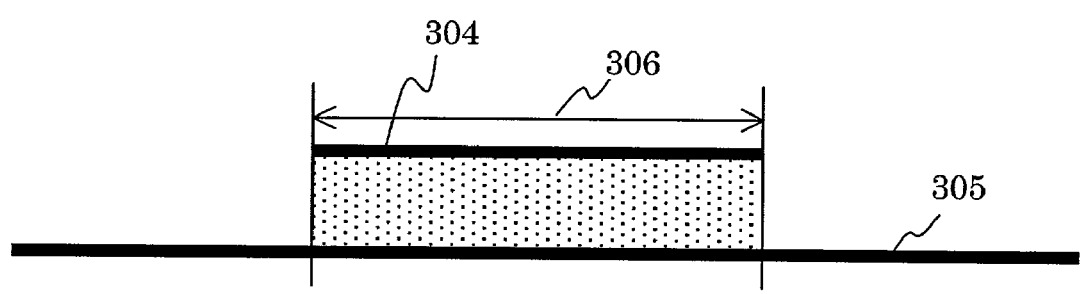

FIG.7
IF ONE COMPUTING WORD IS USED
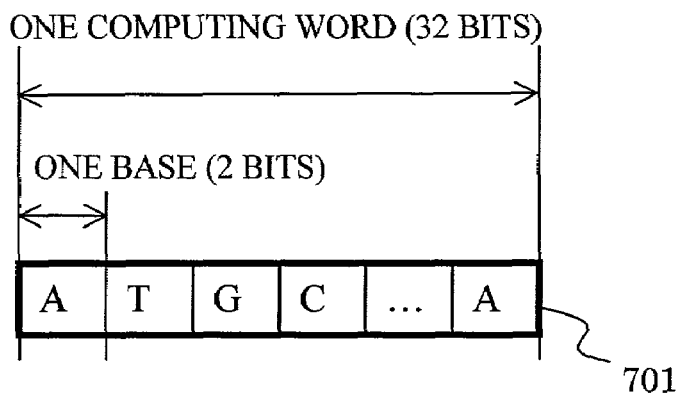
IF TWO COMPUTING WORDS ARE USED
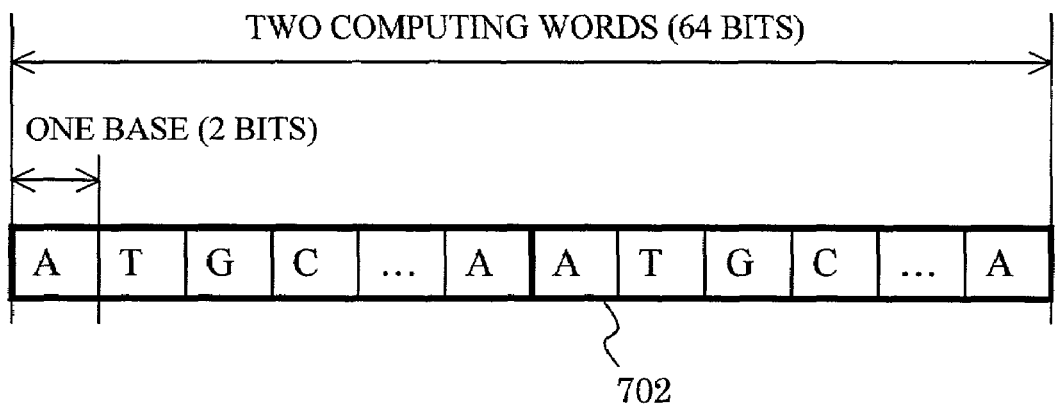

FIG.8
SEQUENCE A:
A1   A2   A3                    101              A4   A5   A6   102
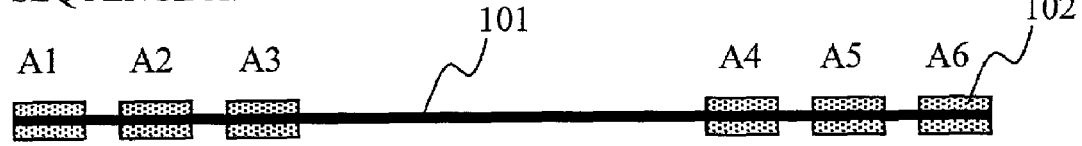
SEQUENCE B:
B1   B2   B3                                     B4   B5   B6
SEQUENCE C:
C1   C2   C3              C4   C5   C6

FIG.10

```
┌─ 1001
│  ┌─ SELECTION OF FIXED LENGTH PARTIAL SEQUENCE POSITION ─┐
│  │  THE NUMBER OF FIXED LENGTH PARTIAL SEQUENCES (K): 6   │ ← 1002
│1021  UPPER LIMIT OF DISTANCE FROM END OF SEQUENCE (R): 63 │ ← 1003
│  │   1004                                    1007         │
│  │     [diagram with R markers]                           │
│  │   1006          1005                                   │
│  └────────────────────────────────────────────────────────┘
│  ┌─ SETTING OF FIXED LENGTH PARTIAL SEQUENCE LENGTH ─┐
│1022 UPPER LIMIT OF EXPECTED VALUE OF THE NUMBER OF    │ ← 1008
│  │  COINCIDENTAL MATCHING OCCURRENCE (c): 0.125       │
│  │  FIXED LENGTH PARTIAL SEQUENCE LENGTH (s): 13      │ ← 1009
│  └────────────────────────────────────────────────────┘
│  ┌─ FIXED LENGTH PARTIAL SEQUENCE KEY FREQUENCY UPPER LIMIT ─┐
│1023  UPPER LIMIT (F): 10    INFINITY ☑ ← 1012
│  │   1011                                                    │
│  │   [graph 1013, 1014]    ATGCA  12345                      │
│  │                         GCAAT     36                      │
│  │                         GGCAC      5                      │
│  │                         TATGG      5  ← 1016              │
│  │                                        1015               │
│  │              1017                                         │
│  └────────────────────────────────────────────────────────────┘
│                    [ OK ] ← 1018   [ Cancel ] ← 1019
```

| A | T | G | C |

1701

| A | T | --> | G | C |

| A | T | A | G | C |

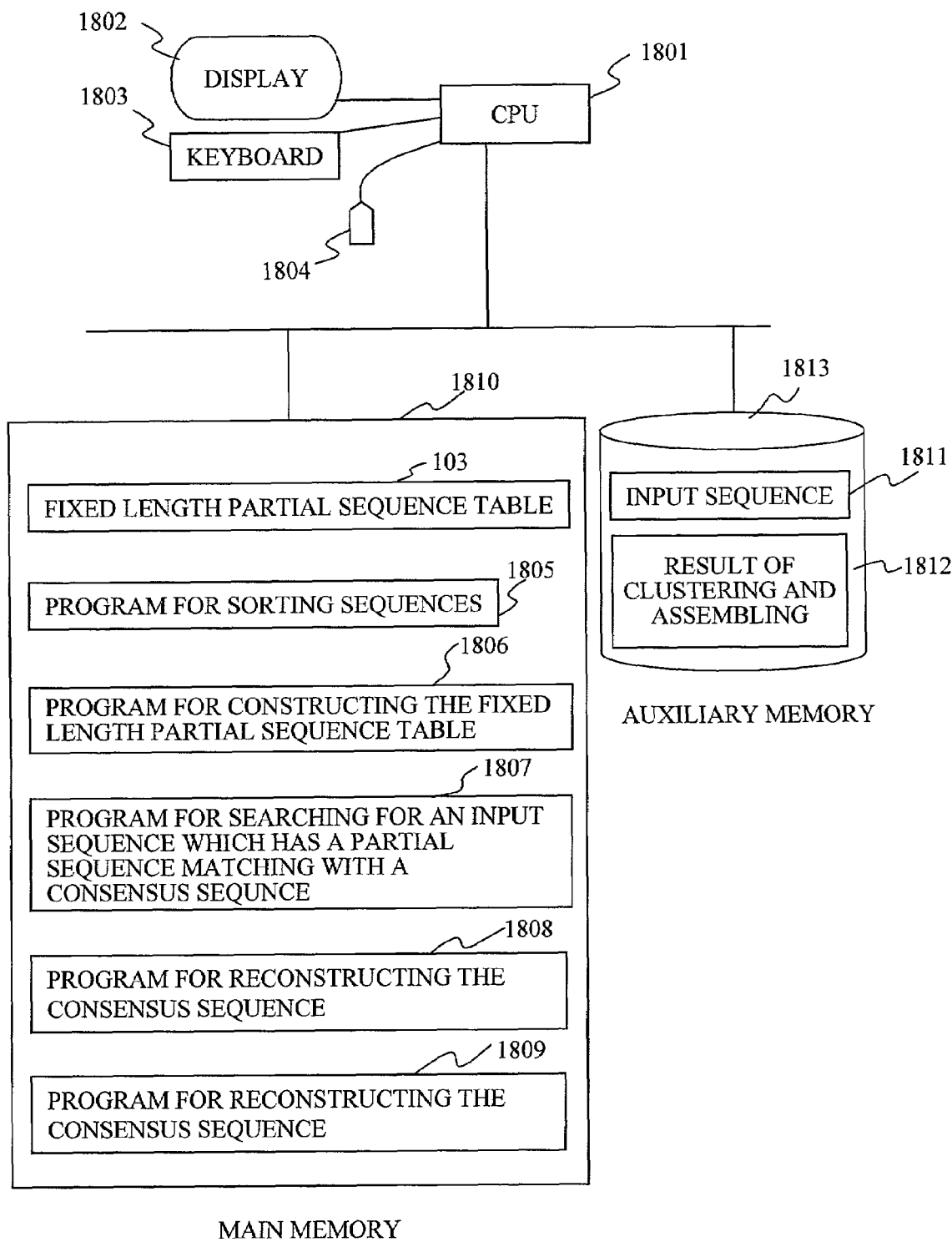

METHOD AND DEVICE FOR ASSEMBLING NUCLEIC ACID BASE SEQUENCES

BACKGROUND OF THE INVENTION

1. Field of the Invention

The present invention relates to a method for clustering and assembling a large number of nucleic acid base sequences at a high speed.

2. Description of the Related Art

The completion of the base sequence determination of human genome has been announced by international joint projects and an U.S. venture company in June of 2000. With improvements in DNA sequence determination technology such as the widespread use of a DNA sequencer utilizing four colors of fluorescent dyes or capillary, complete genome sequences of several tens of varieties of microorganisms including E. coli and S. cerevisiae and multicellular organisms such as C. elegans or D. melanogaster have determined, and draft sequences of the human genome have also become available. In addition, genome projects on various kinds of organisms such as mouse and rice plant are in progress.

While the analysis of the genome sequence proceeds, an analysis of mRNA is also conducted in order to study genes being expressed. mRNA is a sort of RNA which is produced from genome DNA upon gene expression and is a substance which is essential in the course of functional expression of the gene. mRNA which is easily degraded is frequently analyzed in the form of cDNA because mRNA can be easily converted into cDNA, which is more stable than mRNA, through reverse transcription. A sequence obtained by single-pass sequence analysis of cDNA is referred to as an Expressed Sequence Tags (ESTs). ESTs can be utilized for various applications and one of them is to obtain an mRNA sequences.

FIG. 13 schematically illustrates a clustering and assembling processes of the ESTs derived from mRNAs.

When mRNAs are converted into cDNAs 1301, it is difficult to obtain full length cDNAs including 5'-ends, thus the resulting ESTs 1302 based on the cDNAs become sequences in which positions of the 5'-ends usually vary as shown in FIG. 13. When ESTs derived from a cDNA library prepared from all RNAs of a cell or tissue is analyzed, only a set 1303 of ESTs can be obtained. Therefore, it is impossible to know in advance that which mRNA has contributed to a given EST. In a sequence set 1303 made by collecting ESTs 1302, sequences are combined (assembled) to each other based on similar parts 1305 thereof and divided (clustered) into smaller sets as symbolically indicated by arrows 1304. This process allows for identification of ESTs obtained from the same mRNA, and further, sequences 1306 can be obtained having partially reconstructed mRNA sequences.

As for human, it is said that more than a hundred thousand of mRNAs exist corresponding to the number of proteins, so that it is ideal to obtain assemblies corresponding to the respective mRNA sequences by clustering and assembling the input sequence data including ESTs. Presently, about 3.9 million sequences of unprocessed human-originated ESTs and about 1.5 million sequences of human including ESTs partitioned into a set of gene-oriented clusters are stored in a database managed by a U.S. public institution. As a focus of the study shifts to the gene function analysis with the progress of the genome sequence determination, it is expected that the number of sequences derived from mRNA required to be analyzed will be further increased.

The assembling technology is also essential for the genome sequence determination. The determination of genome sequence primarily uses a shotgun method. In the sequence determination by a shotgun method, a long DNA is separated into lots of smaller fragments which are to be cloned, a sequence of each fragment is determined, and the sequence assembling is conducted to determine the entire sequence. For example, a genome sequence of E. coli has about 4639K bases, and its sequence determination by the shot-gun method with a redundancy of 10 usually required requires assembling of $4.639 \times 10^6 \times 10/500 = 9.278 \times 10^5$ sequences, considering that a length of the sequence obtained through a single electrophoresis on a DNA sequencer is about 500 bases. On the other hand, genome sizes of higher organisms such as C. elegans, mice, and humans are greater than that of E. coli by two or three orders of magnitude, so that it is estimated that the number of sequences required for the genome determination will reach a ten million to a hundred million. As the determination of genome sequences of various organisms will be continuously conducted in future, the number of sequences subjected to the assembling is expected to be further increased.

As for the huge number of nucleic acid base sequences, it is difficult in view of a computation time to study the interrelation among respective sequences and to conduct the clustering or assembling thereof. A primary problem in clustering and assembling sequences is how to search for their overlaps between sequences efficiently. If the search for the overlap is simply conducted on all pairs of sequences, it requires to search combinations on the order of the square of the number of sequences, so that an increase in the number of sequences leads to a substantial increase in the processing time. However, the order of entire processing of clustering and assembling is desirable to be extremely lower than the order of the square of the number of sequences.

Among approaches of efficiently searching for an overlap for the clustering and assembling is a method described in Huang, X. and Madan, A., Genome Research, 9:868–877, 1999. However, the number of overlap required to be processed still reaches the order of the square of the number of sequences, so that entire processing of clustering and assembling also reaches the order of the square of the number of sequences. The number of sequences subjected to the clustering and assembling processes has been continuously growing, and it can be expected that the number will further continue to grow.

In view of such problems in the prior art, an object of the present invention is to provide a method and a device for clustering and assembling sequences in a certain computational complexity which is on the order of less than the square of the input sequence number, and for clustering and assembling a large number of nucleic acid base sequences at a high speed.

SUMMARY OF THE INVENTION

The present invention provides a method for assembling nucleic acid base sequences as described below, in order to efficiently search for overlap for clustering and assembling the sequences.

Thus, a method for assembling nucleic acid base sequences according to the present invention comprises the steps of: moving a window of fixed length along a first nucleic acid base sequence and simultaneously searching for a second nucleic acid base sequence which has a partial sequence at a terminal region thereof matching with a sequence defined by the above described window; determining whether the second nucleic acid base sequence searched in the above described step and the first nucleic acid base sequence can be assembled or not; and assembling the first nucleic acid base sequence and the second nucleic acid base sequence if the above described step determines that the second nucleic acid base sequence and the first nucleic acid base sequence can be assembled.

A method for assembling nucleic acid base sequences according to the present invention also comprises the steps of: moving a window of fixed length along a first nucleic acid base sequence and simultaneously searching for a second nucleic acid base sequence which has a partial sequence at a terminal region thereof matching with a sequence defined by the above described window; determining whether the second nucleic acid base sequence searched in the above described step and the first nucleic acid base sequence can be assembled or not; and the first nucleic acid base sequence and the second nucleic acid base sequence are assembled if the above described step determines that the second nucleic acid base sequence and the first nucleic acid base sequence can be assembled, in which the nucleic acid base sequence assembled in the above described step is used as a new first nucleic acid base sequence to repeatedly carry out the above described steps.

A method for assembling nucleic acid sequences according to the present invention also comprises the steps of: entering identification information about each of a plurality of nucleic acid base sequences and a fixed-length partial sequence located in a terminal region of the above described nucleic acid base sequence into a table, both of which are associated with each other; constructing a first consensus sequence based on a first sequence; searching for a nucleic acid base sequence which has a partial sequence matching with a part of the consensus sequence with reference to the table; comparing a sequence adjacent to the above described partial sequence of the nucleic acid base sequence searched in the above described step with a sequence adjacent to the above described partial sequence of the consensus sequence, and determining whether the searched nucleic acid base sequence can be assembled to the consensus sequence or not; and, if the above described step determines that the searched nucleic acid base sequence can be assembled to the consensus sequence, assembling the above described nucleic acid base sequence to the consensus sequence so as to reconstruct a consensus sequence.

As a first sequence for constructing the first consensus sequence, a sequence whose base length is the longest among the unprocessed nucleic acid base sequences is selected. Preferably, an entry which is related to a nucleic acid base sequence assembled to the consensus sequence is deleted from the table after each assembling.

A method for assembling nucleic acid base sequences according to the present invention also comprises: a first step of sorting a plurality of nucleic acid base sequences in descending order of their sequence lengths; a second step of entering identification information about each of the plurality of nucleic acid base sequences and a fixed-length partial sequence located in a terminal region of the above described nucleic acid base sequences into a table, both of which are associated with each other; a third step of selecting one of the nucleic acid base sequences whose sequence length is the longest among the plurality of unprocessed nucleic acid base sequences and constructing a consensus sequence; a fourth step of moving a fixed length window along the consensus sequence and simultaneously searching for an unprocessed nucleic acid base sequence which has a partial sequence matching with a sequence defined by the fixed length window with reference to the table; a fifth step of comparing the consensus sequence with the unprocessed nucleic acid base sequence searched in the fourth step, and determining whether the both sequences can be assembled or not; and a sixth step of, if the fifth step determines that the both sequences can be assembled, assembling the nucleic acid base sequence searched in the fourth step to the consensus sequence so as to reconstruct a consensus sequence, in which the fourth step to the sixth step are repeated until the fixed length window completes the scanning throughout the consensus sequence, and the third step to the sixth step are repeated if unprocessed nucleic acid base sequences still remain.

The above-described method can comprise a step for specifying the number of the fixed-length partial sequences to be entered into the above-described table, for one nucleic acid base sequence.

Also, the above described method can comprise a step of designating a range of the terminal region of the nucleic acid base sequence from which the fixed base length of partial sequence to be entered into the above described table is extracted.

A base length of the fixed base length of partial sequence to be entered into the above described table is preferably at least 10 bases or more and preferably 32 bases or less which can be represented by two words in case of a computer using a 32 bit-word and also represented by one word in case of a 64-bit computer, because it requires to minimize the number of entries which are independent of the overlaps between sequences detected at the time of table reference in order to prevent a decrease in processing speeds.

More preferably, the above described method comprises a step of specifying an upper limit c to an expected value of the number of entries which are searched upon once referencing the above described table and determined not to be able to assemble to the consensus sequences, in which if the number of the plurality of nucleic acid base sequences is N and the number of the fixed base length of partial sequences selected from each nucleic acid base sequence is K, an integer s satisfying the following expression (1) is the base length of the fixed base length of partial sequence to be entered into the above described table.

Preferably, a two-way list is used for a data structure storing the consensus sequences.

It is also preferable to represent the fixed base length of partial sequence by the fixed number of computing words which are independent of a length of the above described fixed base length partial sequence. A result of clustering is preferably outputted after each completion of the clustering, without accumulating the result in a main memory of the computer.

Further, it is preferable to utilize only entries corresponding to a partial sequence which occurs a previously specified number of times or less in the above described table.

The present invention also provides a graphical user interface for conducting selection of the input sequence required for conducting the assembling (clustering) process according to the above described method, input of parameters, display of the progress of the clustering and assembling processes, and display of the result.

A device for assembling nucleic acid base sequences according to the present invention comprises: input means for inputting parameters associated with a fixed-length partial sequence which is set in a terminal region of each input nucleic acid base sequence; means for entering identification information about each of a plurality of input nucleic acid base sequences and a fixed-length partial sequence extracted from the above described nucleic acid base sequences based on the parameter input by the input means into a table, both of which are associated with each other; means for searching for a nucleic acid base sequence which has a partial sequence matching with a part of a consensus sequence with reference to the above described table; determination means for comparing the nucleic acid base sequence searched in the above described step with the consensus sequence, and determining whether the both sequences can be assembled or not; and means for assembling the consensus sequence and the searched nucleic acid base sequence so as to reconstruct a consensus sequence if the determination means determines that the both sequences can be assembled.

The input means may have a display for graphically displaying positions of the fixed-length partial sequences in the input nucleic acid base sequence relative to terminals of the sequences so that a position of a fixed-length partial sequence specified by a user can be immediately reflected on the display.

In addition, the input means may input the number of fixed-length partial sequences to be extracted for one input nucleic acid base sequence and the length of them.

The input means may also specify the length of fixed-length partial sequences to be entered into the above described table, based on the expected value of the number of coincidences detected at the time of referencing the above described table.

Preferably, the device for assembling the nucleic acid base sequences has a display for displaying graphics and/or numerical values representing the frequency of occurrence of each of the fixed-length partial sequence entered into the above described table. In addition, the device preferably comprises means for specifying an upper limit of the frequency of occurrence and means for deleting an entry whose frequency of occurrence is beyond the upper limit specified from the above-described table.

Further, the device preferably comprises means for displaying each input nucleic acid base sequence assembled to the consensus sequence together with a position of the fixed-length partial sequence in the input nucleic acid base sequence matching with a part of the consensus sequence.

BRIEF DESCRIPTION OF THE DRAWINGS

FIG. 3 shows the reason why partial sequences located at a head end and at a tail end are entered into a fixed-length partial sequence table;

FIG. 7 represents an example of encoding a fixed-length partial sequence in a few computer words;

FIG. 8 shows a method for extracting a plurality of partial sequences from a head end and a tail end of each sequence at the time of preparing the fixed-length partial sequence table;

FIG. 10 shows an example of an input interface;

FIG. 18 shows an example of a configuration of a device for assembling nucleic acid base sequences according to the present invention.

DETAILED DESCRIPTION OF THE PREFERRED EMBODIMENTS

An embodiment of the present invention will be described below with reference to drawings.

Figure 1:
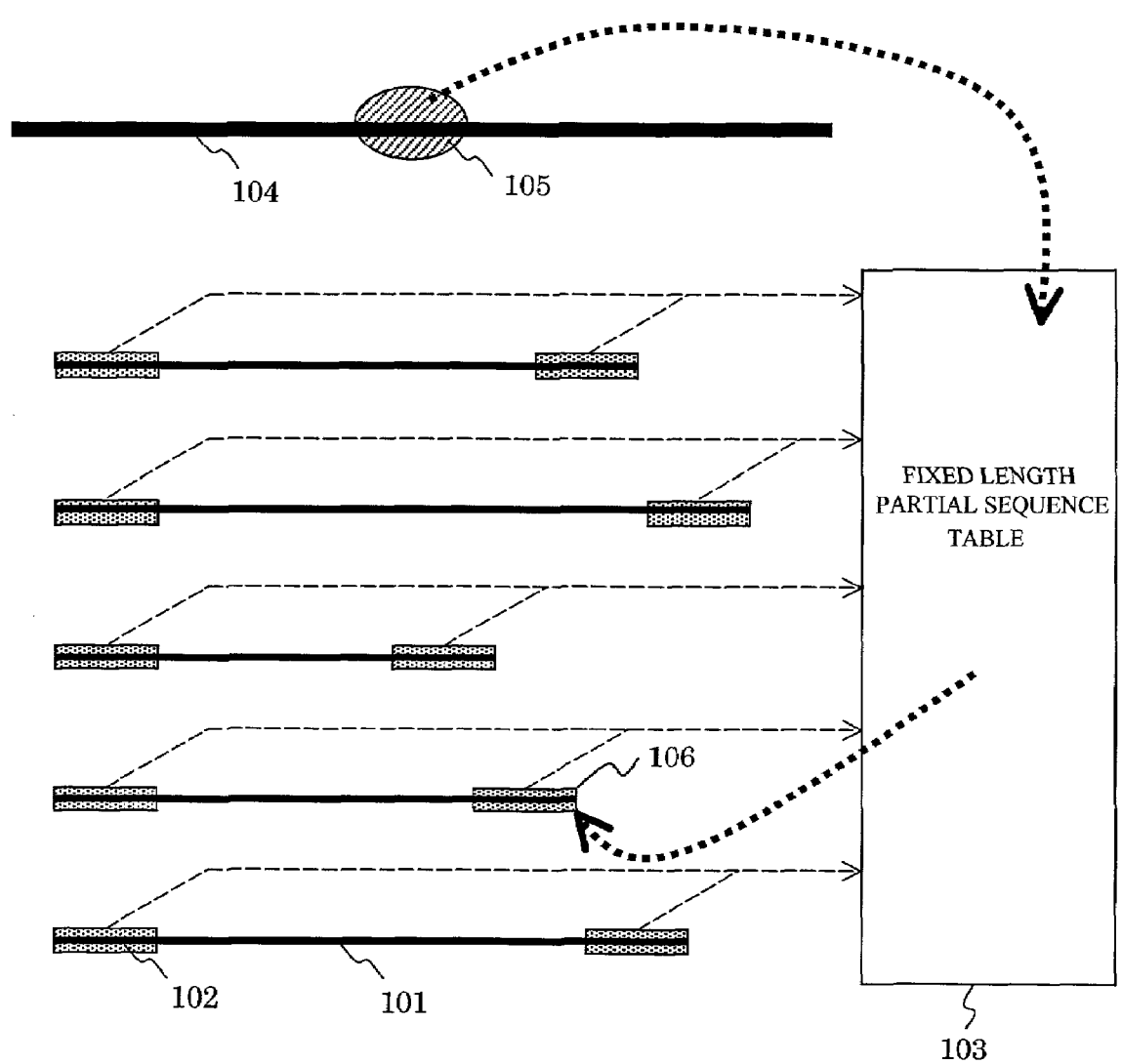
FIG. 1 represents a basic idea of the present invention.

In a clustering and assembling method according to the present invention, we have focused on a property of an overlap between sequences. As shown in FIG. 3, overlapping portions 303, 306 between two sequences necessarily include tail end portions of one sequences (a sequence 301 and a sequence 304 in FIG. 3) and head end portions of the other or the same sequences (a sequence 302 and a sequence 304). In the present invention, as shown in FIG. 1, a partial sequence 102 having a length of s positioned at each of a head end and a tail end of an input sequence 101 is stored in a fixed-length partial sequence table 103. A method for determining the length value s will be described later. This fixed-length partial sequence table 103 is referred in order to check whether an input sequence overlapped with a certain sequence is present or not. When it has been found that a partial sequence 106 of a certain input sequence completely matches with a sequence defined by a fixed length window 105 as a result of referring to the table, whether it is included or not in the same cluster is verified by the detailed comparison of the sequences at the overlapping portion. Then members are included in the cluster one after another, based on a greedy method.

Figure 2:
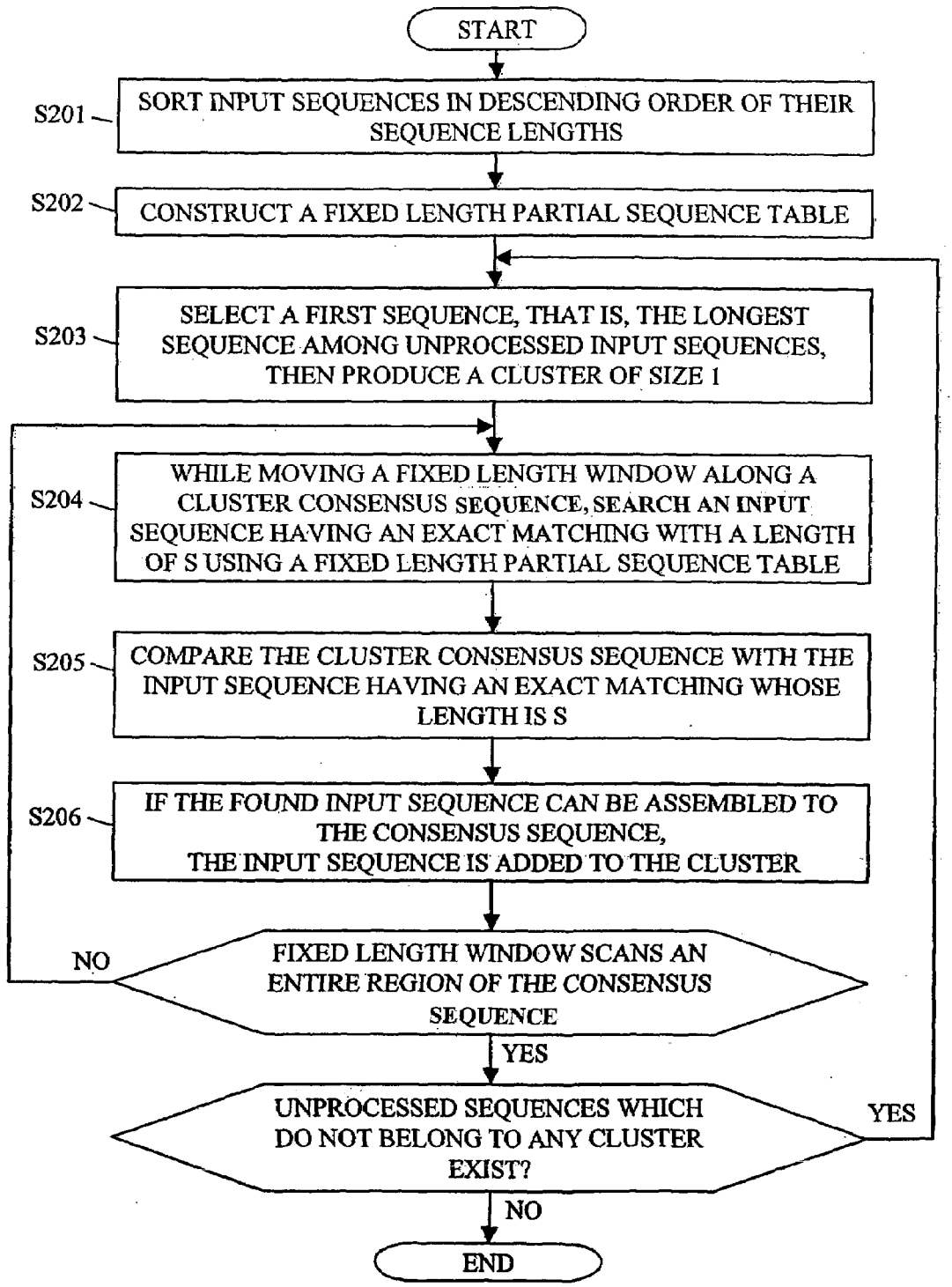
FIG. 2 is a flowchart showing a general flow of a clustering and assembling method according to the present invention.

Now a method according to the present invention will be described. FIG. 2 shows a flowchart of the processing.

First, as shown in FIG. 2, input sequences are sorted in descending order of their sequence lengths. This allows for avoidance of a certain situation in which, when the overlapping portion between the sequence 304 and the sequence 305 is searched as can be seen in FIG. 3, the sequence 304 and the sequence 305 cannot be linked together because the sequence 304 does not have a partial sequence matching with a head end or a tail end of the sequence 305.

Figure 4:
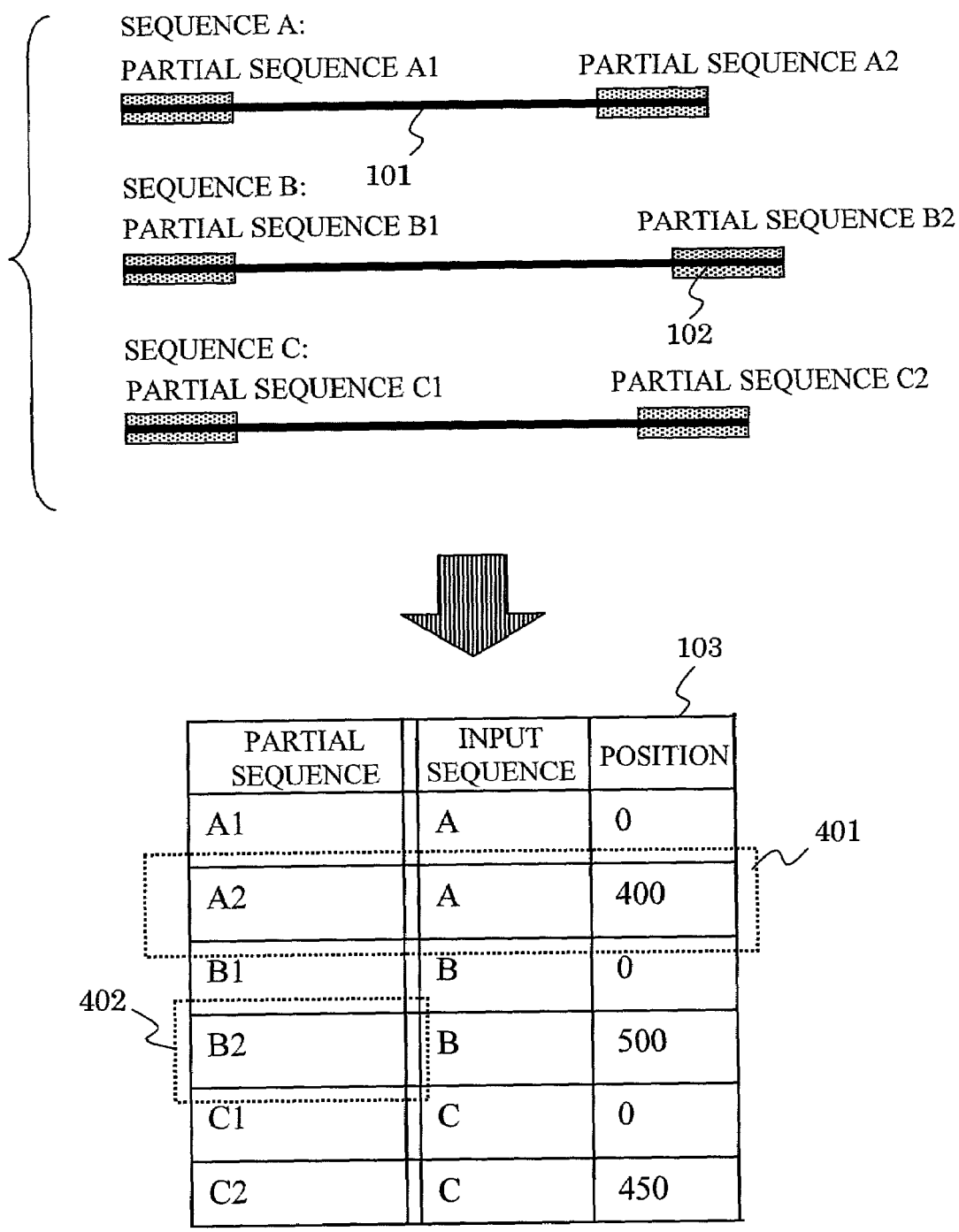
FIG. 4 shows a method for constructing the fixed-length partial sequence table.

Next, the process proceeds to Step 202 in FIG. 2 and constructs a fixed-length partial sequence table 103. When constructing the fixed-length partial sequence table 103, partial sequences 102 having a length of s at the head and tail ends of all the input sequences 101 is entered into the table 103 as shown in FIG. 4. If the length s of the partial sequence is taken longer, the probability of occurrence of coincidence between the lengths s can be decreased regardless of the presence of a true overlap between the input sequences, so that the processing time can be shorten. However, if the length s of the partial sequence is excessively taken too long, the sensitivity for searching for an overlap will become lower. In the present invention, the value s has a lower limit which is represented by an expression (1) described below, in order to shorten the processing time.

$$s \geq \frac{1}{2} \log \frac{KN}{c} \quad (1)$$

In the above expression (1), N is the number of input sequences, K is the number of partial sequences selected from each sequence, and c is a parameter given by a user and is an amount specifying an upper limit of the expected value of the number of exact matching which can be found after each reference to the fixed-length partial sequence table 103 regardless of the presence of the true overlap between the input sequences. If the value c becomes larger, the value s can be smaller. Thus the length of the partial sequence becomes shorter, so that the sensitivity for searching for an overlap can be higher. However, the computing time for processing the coincidence matching becomes longer, so that the processing speed decreases. In this specification, the base of logarithms is 2.

When the partial sequence is entered into the fixed-length partial sequence table 103, identification information about the input sequence including the partial sequence and its position in the input sequence are simultaneously stored. Each set of three values, that is, the partial sequence, the input sequence identification information and the position in the input sequences as shown in FIG. 4, is called an entry. In addition, each of the partial sequence indicated by reference numeral 402 in FIG. 4 is called a key. Each entry in the fixed-length partial sequence table 103 can be extracted by reference to the table 103 using a base sequence having a length of s matching as a key. For implementation of the fixed-length partial sequence table 103, a balanced-tree which is a binary-tree such as an AVL-tree is used (G. M. Adel'son-Vel'skii and E. M. Landis, "An algorithm for the organization of information", Soviet Mathematics Doklady, 3:1259–1263, 1962).

After entering the partial sequences from the input sequences, every entry which corresponds to a key having the frequency of occurrence beyond a parameter F (described later) given by the user is deleted from the fixed-length partial sequence table 103. Generally, a nucleic acid base sequence often includes repeated sequences, so that it is expected that a lot of matching between partial sequences of the lengths s which are independent of the true overlap between input sequences may be found. Therefore, this processing intends to delete an entry corresponding to a key whose frequency of occurrence is extremely high.

After constructing the fixed-length partial sequence table 103, the process proceeds to Step 203 in FIG. 2 and constructs individual clusters. First, the longest input sequence is selected, and a cluster of size 1 is configured. Because of Step 201 for sorting, the longest input sequence can be easily selected within constant time only by selecting a firstly appeared input sequence. A consensus sequence 104 of the cluster is constructed by replicating the same sequence as the longest input sequence selected. On this consensus sequence, a fixed length window 105 having a width s is provided.

A method for adding a new member to the cluster will be described below with reference to FIG. 5. As for the cluster which has constructed until then, the fixed length window 105 having a width s is allowed to move through the whole consensus sequence 104 of the cluster. While moving the window, the fixed-length partial sequence table 103 is referred to by using the partial sequence defined by the window as a key, and a candidate for the input sequence which becomes a potential member of the cluster is searched (Step 204 in FIG. 2).

Suppose that an exact matching 501 with a certain input sequence 502 is found when referring to the fixed-length partial sequence table 103. Only the occurrence of the exact matching 501 having a length of s is not sufficient as a condition for adding this sequence 502 to the cluster because this exact matching may occur merely by coincidence. Therefore, it should be verified that both of the entire overlapping portions 503 are sufficiently similar to each other and the assembling is possible without contradiction between them by comparing one sequence with the other (Step 205 in FIG. 2). In this sequence comparison, a position of the exact matching whose length is s between the consensus sequence and the input sequence is apparent, so that a high speed algorithm described in Zhang, Z. et al., J. Comput. Biol., 7 (1–2): 203–14, 2000 is used.

First, we show a procedure that compares two nucleic acid sequences and calculates information to get scores of alignments that indicate how similar the compared sequences are.

---

1. $i \leftarrow 0$
2. while $i < \min\{M,N\}$ and $a_{i+1} = b_{i+1}$ do $i \leftarrow i + 1$
3. $R(0,0) \leftarrow i$
4. $T^i \leftarrow T[0] \leftarrow S^i(i + i, 0)$
5. $d \leftarrow L \leftarrow U \leftarrow 0$
6. repeat
7. $\quad d \leftarrow d + 1$
8. $\quad d^1 \leftarrow d - \left\lfloor \dfrac{x + \text{mat}/2}{\text{mat} - \text{mis}} \right\rfloor - 1$
9. $\quad$ for $k \leftarrow L - 1$ to $U + 1$ do
10. $\quad\quad i \leftarrow \max \begin{cases} R(d-1, k-1) + |1 & \text{if } L < k \\ R(d-1, k) + 1 & \text{if } L \leq k \leq U \\ R(d-1, k+1) & \text{if } k < U \end{cases}$
11. $\quad\quad j \leftarrow i - k$
12. $\quad\quad$ if $i > -\infty$ and $S^i(i + j, d) \geq T[d^i] - X$ then
13. $\quad\quad\quad$ while $i < M$, $J < N$ and $a_{i+1} = b_{j+1}$ do
14. $\quad\quad\quad\quad i \leftarrow i + 1;\ j \leftarrow j + 1$
15. $\quad\quad\quad R(d, k) \leftarrow i$
16. $\quad\quad\quad T^i \leftarrow \max\{T^i, S^i + j, d)\}$
17. $\quad\quad$ else $R(d, k) \leftarrow -\infty$
18. $\quad\quad T[d] \leftarrow T^i$
19. $\quad L \leftarrow \min\{k : R(d, k) > -\infty\}$
20. $\quad U \leftarrow \max\{k : R(d, k) > -\infty\}$
21. $\quad L \leftarrow \max\{L, \max\{k : R(d, k) = N + k\} + 2\}$
22. $\quad U \leftarrow \min\{U, \min\{k : R(d, k) = M\} - 2\}$
23. until $L > U + 2$
24. report $T^i$

---

This procedure is exactly the same as the one in FIG. 4 of Zhang et al, 2000. Notations in this procedure mean the following:

M Length of the first nucleic acid sequence compared.
N Length of the second nucleic acid sequence compared.
i Index that points a base in the first nucleic acid sequence compared.
j Index that points a base in the second nucleic acid sequence compared.
$a_i$ $i^{th}$ base of the first sequence compared.
$b_j$ $j^{th}$ base of the second sequence compared.
k Variable that represents i-j.
d Number of differences of two compared sequences found so far.

d' Number of differences of two compared sequences to be used to prune away bad alignments.

Mat Score given to alignment of each pair of bases that are identical.

mis Score given to alignment of each pair of bases that are not identical.

R(d,k) 2-dimensional variable. This procedure sets R(d,k) to the largest i such that the best alignment of $a_1 a_2 \ldots a_i$ and $b_1 b_2 \ldots b_{k-i}$ had d differences.

T[x] Variable to be used to prune away bad alignments.

L Lower limit of k to which the alignment can be extended.

U Upper limit of k to which the alignment can be extended.

The result of the comparison is set to R (d,k). Besides, we can retain $d_{best}$ and $k_{best}$, the values of variables d and k when the maximum value of T' is first assigned (line 16), which also appears in Zhang, et al. 2000.

With R (d,k), $d_{best}$, and $k_{best}$, we can obtain a sequence of operations so called edit script by the following procedure.

procedure script(d, k)

```
if d>0then
   i←max{R(d-1,k-1)+1,R(d-1,k)+1,R(d-1,R(d-1,k+1)}
   if i=R(d-1,k-1)+then
      script(d-1,k-1)
      print "delete a_i"
   else if i=R(d-1,k)+1 then
      script(d-1,k)
      print "replace a_i" byb_{i-k}"
   else
      script(d-1,k)+1)
      print "insert a_{i-k}"
```

Figure 5:
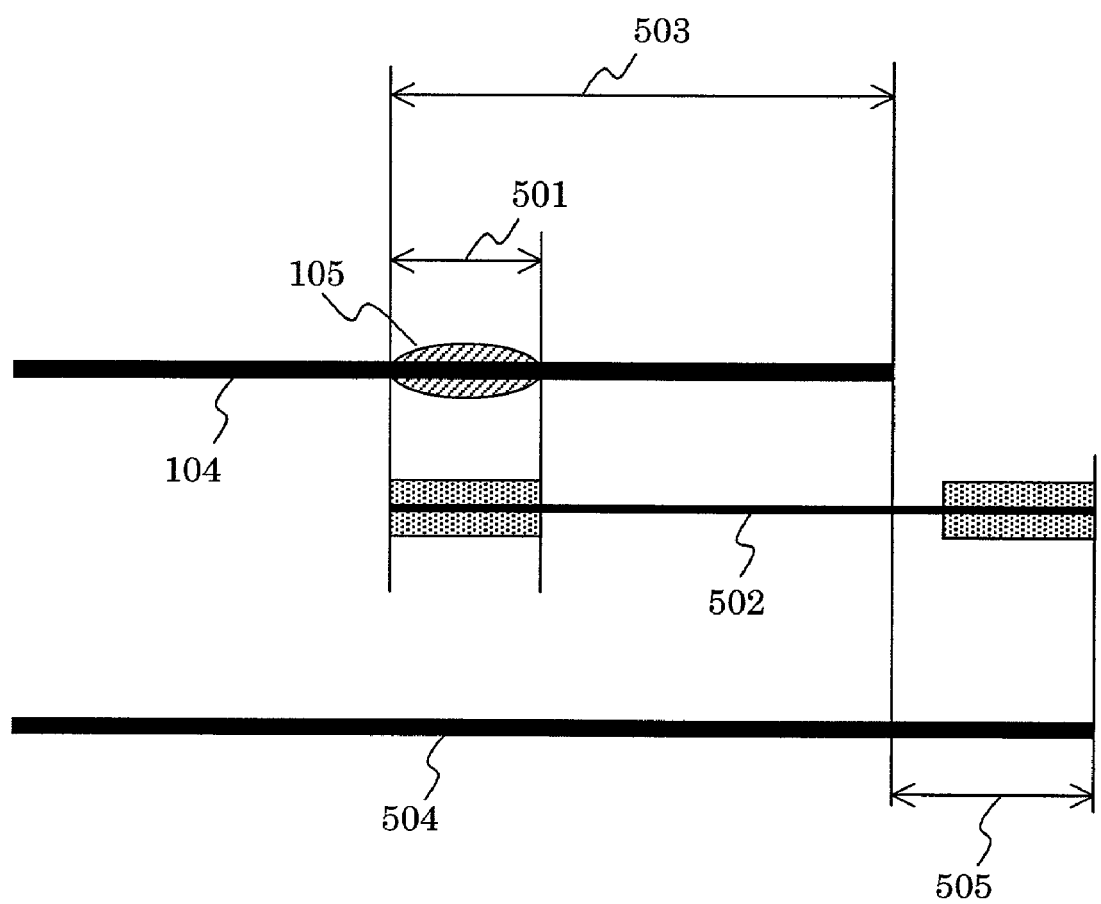
FIG. 5 shows a sequence overlapping status when adding a new member, that is, a new input sequence to a cluster.

This procedure is exactly the same as the one in FIG. 5 of Zhang et al, 2000. The edit is like "delete $a_5$, replace $a_5$ by $b_1$, insert $b_{10} \ldots$". With an edit script, we can obtain the best alignment of two sequences compared, which enables us to calculate the identity of the sequences and to assemble them.

If it is determined by the sequence comparison of Step 205 that both sequences within the entire overlapping portions 503 are well similar to each other, the input sequence 502 is added to the cluster and the consensus sequence 104 is also modified into a new consensus sequence 504 (Step 206 in FIG. 2). An extended portion 505 of the consensus sequence is also included within a moving area of the fixed length window 105 having a width of s. An entry in the fixed-length partial sequence table 103, which is associated with the input sequence 502 being added to the cluster, is deleted.

Figure 6:
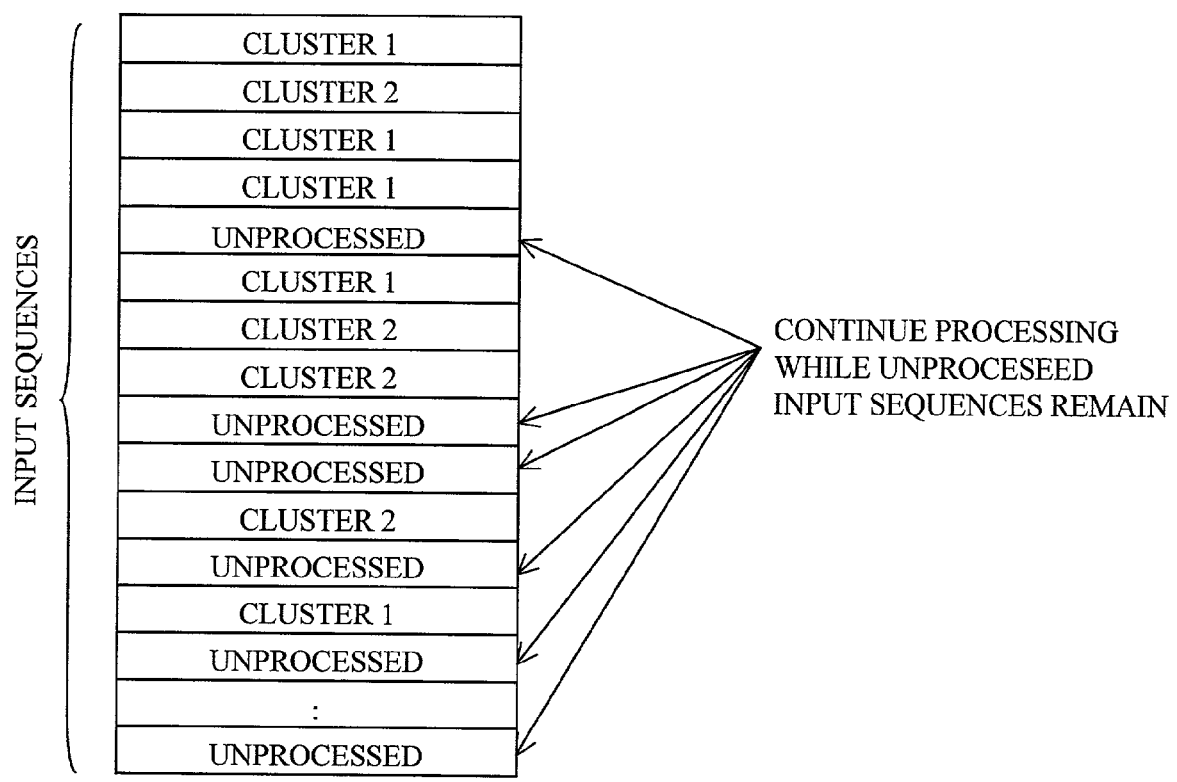
FIG. 6 represents the process of a method according to the present invention.

The same process is repeated during the moving area of the fixed length window 105 remains on the consensus sequence 104. A completed cluster is sequentially output to a file etc. and does not remain in a memory of the computer. This process is repeated while the unprocessed sequences which do not belong to any cluster remain as shown in FIG. 6.

This is a main flow of the method of the present invention. In addition to the above description, the method of the present invention has characteristics as follows for conducting a high speed processing.

Figure 14:
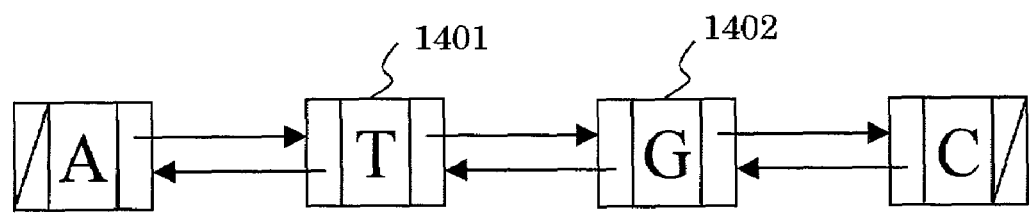
FIG. 14 shows a method for storing base sequences by using a two-way list as a data structure.
Figure 15:
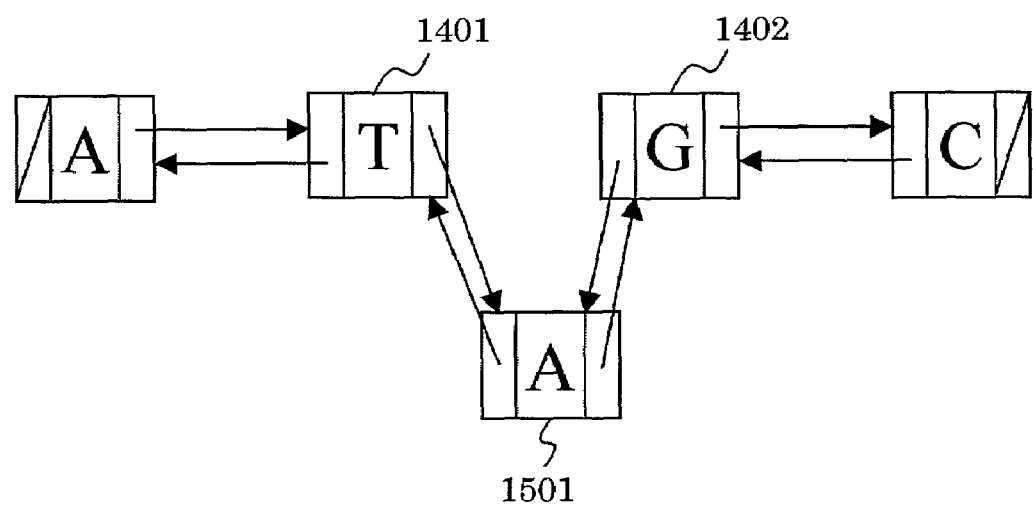
FIG. 15 shows a method for inserting a new base into a base sequence which is stored in a two-way list.
Figures 16, 17:
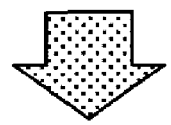
FIG. 16 shows a method for storing a base sequence in an array.
FIG. 17 shows a method for inserting a new base into a base sequence stored in an array.

First, two-way list are used to implement consensus sequences 104 (FIG. 14). As for a sequence shown in FIG. 14, if it becomes necessary to newly insert a base A 1501 between a base T 1401 and a base G 1402, pointers adhered between the base T 1401 and the base G 1402 are removed and adhered towards the base A 1501. On the other hand, from the base A 1501, new pointers can be adhered toward the base T 1401 and the base G 1402 respectively as shown in FIG. 15. This processing can be conducted within constant time. If the consensus sequence is implemented by the use of a data structure using adjacent memory locations, that is, an array as shown in FIG. 16, it becomes necessary to shift the bases, which are located in a rearward position of a position into which a new base is inserted, toward the rear and to insert the new base A into the created gap 1701 in order to insert one base. Thus an average of the processing time becomes an amount proportional to the sequence length. At the time of sequence comparison, in order to allow each random access to be conducted within constant time, only a sequence region of the consensus sequence 104 which requires to be subjected to the comparison is copied onto a region of an array-like data structure, that is, a continuous main memory. The length of the sequence region copied at this time is below the sum of a value which is obtained by doubling the maximum number of gaps accepted at the time of sequence comparison and a sequence length of the input sequence. On the continuous memory region, random access for any base is achieved within constant time because only a multiplication and an addition can be performed as for a position into which a base of the sequence is stored.

Also, the method of the present invention subjects a sequence whose length is s to the comparison conducted within constant time by encoding a partial sequence having a length of s into a few computing words. FIG. 7 shows an example in the case of a 32 bit-word computer. A sequence having 16 bases or less can be encoded if one computing word 701 is used, and a sequence having 32 bases or less can be encoded if two computing words 702 are used. If characters other than A, T, G, and C exist, those characters are forcefully assumed to be identical to any of the characters A, T, G, and C, then encoded.

Further, the clustering and assembling method according to the present invention allows for clustering in which minor errors of bases are acceptable by entering not only two partial sequences at both ends of the input sequence but also more than two partial sequences of the input sequence into the fixed-length partial sequence table 103, in order to deal with sequencing errors which may occur in nucleic acid base sequences. Since the partial sequence located near the end of the input sequence becomes important for searching for an overlap, K partial sequences in total are selected from an area within R bases of each end of the sequence (R is a user parameter) and entered into the fixed-length partial sequence table 103. According to this method, even if errors occur in a certain partial sequence, it becomes possible to find the overlap based on the other partial sequence. FIGS. 1 and 4 show an example in which K=2, and FIG. 8 shows an example in which K=6.

The clustering and assemble method according to the present invention has been schematically described. Now, we will describe through theoretical consideration that this method is a clustering and assembling method actually performed at a high speed and consumed main memory of the computer are also limited. The description below will use the symbols as follows.

N: the number of total input sequences

D: the number of total bases of an input sequence $L_i$: The length of the consensus sequence at the time of completing the clustering of a certain cluster i $N_i$: the number of cluster members at the time of completing the clustering of a certain cluster i L: a sum of lengths of consensus sequences of all clusters at the time of completing the clustering L': The length of the longest consensus sequence among all clusters at the time of completing the clustering n: the number of clusters at the time of completing the clustering $D_{ij}$: The length of an input sequence of the cluster i, which is added as j th member.

M: The length of the longest input sequence

E: The expected value of the number of entries which are coincidentally found despite lack of an overlapping portion between the input sequences, after each reference to a fixed-length partial sequence table 103

K: the number of partial sequences entered into a fixed-length partial sequence table 103 from one input sequence c: a user parameter for setting an upper limit of E Notation using a capital O which is used in the present invention for representing a computing time and an amount of consumed main memory is described in D. E. Knuth, "The O-notation in Fundamental Algorithms—The Art of Computer Programming" Second Edition, pp. 104–108, Addison-Wesley publishing company, ISBN0-201-03821-8, 1973.

Now, high speed performance achieved by the method of the present invention will be described, supposing that the input sequence data is a random sequence of four kinds of bases including A, T, G, and C bases. First, a time which is required to sort the input sequences in descending order of their sequence lengths is O(D+N log N). This is because a time of O(D) is required to determine the sequence length. If a quick sort or a merge sort is used, the sorting processing can be completed within O(N log N).

Next, according to the method of the present invention, a time required for configuring the fixed-length partial sequence table 103 is O(KN log N). This is because the computing time for entering all partial sequences is O(KN log(KN)) since a balanced binary tree which is a binary-tree is utilized for the implementation of the fixed-length partial sequence table 103. If N is sufficiently larger than N(N≧K), the computing time becomes O(KN log N). Also, the deletion of entries corresponding to a key whose frequency of occurrence is beyond F can be conducted within O(KN log N).

Further, according to the method of the present invention, a time required for constructing the i th cluster only is expressed by the following expression (2).

$$O\left((L_i + N_i)\log N + L_i E(M + \log N) + \sum_{j=1}^{N_i} D_{ij} + KN_i \log N\right) \quad (2)$$

This is because the details of the processing time when constructing only the i th cluster becomes as follows.

1. The computation time required for processing, in which one input sequences is selected and a consensus sequence is constructed, is on the order of a length of the input sequence.

2. The computation time required for processing in which the fixed-length partial sequence table 103 is referred is $O((L_i+N_i-1+L_iE)\log N)$. This is because, firstly, a time required for processing in which the fixed-length partial sequence table 103 is referred one time is O(log N). Next, an expected value of the number of making the reference will be discussed. The reference should be made at least $O(L_i)$ times corresponding to the consensus sequence length. If matching with a true overlap between the input sequences is concentrated on the same position of the consensus sequence, the reference should be made further $O(N_i-1)$ times. Aside from this, an expected value of the number of finding a coincidental matching is $O(L_iE)$. Therefore, the expected value of the number of making reference becomes $O(L_i+(N_i-1)+L_iE)$.

3. If an input sequence which can be added to the cluster is found as a result of referring to the fixed-length partial sequence table 103 and conducting the detailed sequence comparison, as for the j th input sequence, computation time required for the sequence comparison based on the above described high speed algorithm and the consensus sequence update is $O(D_{ij})$, and a computing time required for processing in which an entry associated with the input sequence in the fixed-length partial sequence table 103 is deleted is $O(KN_1 \log N)$, so that the computing time required in total becomes $O(D_{ij}+KN_i \log N)$.

4. If a coincidental matching independent of the overlapping portion between sequences is found as a result of making reference to the fixed-length partial sequence table 103, O(M)-time is required for performing the sequence comparison based on the above described high speed algorithm after each finding of such a coincidental matching.

Therefore, the computing time required for entire processing of constructing one cluster is proved to be expressed by the above expression (2) through the following expression (3).

$$O(D_{i1}) + O\left((L_i + (N_i - 1) + L_i E)\log N\right) + \qquad (3)$$
$$\sum_{j=2}^{N_i} O(D_{ij} + K \log N) + O(L_i EM) =$$
$$O\left(D_{i1} + (L_i + N_i - 1 + L_i E)\log N + \sum_{j=2}^{N_i} D_{ij} + L_i EM + KN_i \log N\right) =$$
$$O\left((L_i + N_i)\log N + L_i E(M + \log N) + \sum_{j=1}^{N_i} D_{ij} + KN_i \log N\right)$$

Therefore, a total computing time for computing all clusters is O((L+N)log N+LE(M+log N)+D+KN log N) from the following expression (4).

$$\sum_{i=1}^{n}\left[O\left((L_i + N_i)\log N + L_i E(M + \log N) + \sum_{j=1}^{N_i} D_{ij} + KN_i \log N\right)\right] = \qquad (4)$$
$$O((L + N)\log N + LE(M + \log N) + D + KN \log N)$$

Considering two points, that is, NK/4^s≦c is established because s satisfies an expression (1) and E≦KN/4^s (4^s represents 4 to the s th power) is established because sequences are supposed to be random, an expression $E \leq c$ is established.

Therefore, computation time required for computing all clusters becomes $O(D(M+\log N))$ by transforming $O((L+N)\log N+LE(M+\log N)+D+KN \log N)$ with the use of L, N, $KN \leq D$.

Both of $O(D+N \log N)$-time for sorting and $O(D \log N)$-time for configuring the fixed-length partial sequence table 103 can be included in $O(D(M+\log N))$-time, so that the total computation time required for the clustering and assemble method of the present invention becomes $O(D(M+\log N))$.

If all sequences has the same length M and hence $D=NM$, a total computing time required for the method of the present invention is $O(MN(M+\log N))$. In this expression, M is a sequence length and is also an amount independent of N. Therefore, when N increases, computation time required for the method of the present invention only increases on the order of N log N, far less than the square of N. That is, according to the method of the present invention, an object of performing clustering and assembling on the order of less than the square of the number of sequences has been achieved.

On the other hand, the main memory which is consumed by the method of the present invention, excluding the input sequence data and the cluster information to be output, is $O(KN+L')$. The main memory required for storing the fixed-length partial sequence table 103 is $O(KN)$ in case of using a binary-tree, and the cluster information being processed becomes $O(L')$ because this information is suppressed by the sum of the sequence lengths of respective members. In addition, only $O(1)$ memory is required for other purposes. $O(KN+L')$ does not depend on the length of the input sequence and is an amount which only increases on the order proportional to the number of sequences.

FIG. 18 is a block diagram showing an example of a configuration of a device for assembling nucleic acid base sequences which performs the above-described method. As shown in FIG. 18, the device for assembling nucleic acid base sequences of the present invention comprise a CPU 1801 for performing calculation, a display 1802 for displaying an interface, a keyboard 1803, and a pointing device 1804, and further comprises a main memory 1810 storing a program 1805 for sorting the input sequences in descending order of their sequence lengths, a program 1806 for constructing a fixed-length partial sequence table 103, a program 1807 for searching for the input sequence having a partial sequence matching with a consensus sequence, a program 1808 for determining whether the consensus sequence and the input sequence can be assembled together, a program 1809 for reconstructing the consensus sequence, and the fixed-length partial sequence table 103, as well as an storage devices 1813 which can store the input sequence 1811 and a result of clustering and assembling 1812 therein.

After input sequences and parameters required for the method of the present invention are specified by the display 1802, the keyboard 1803, and the pointing device 1804, the CPU 1801 executes the program stored in the main memory 1810 and the clustering and assembling are performed by the method of the present invention. The input sequence 1811 is read from the storage devices 1813. The output result of clustering and assembling 1812 can be stored into the storage devices 1813. During the progress of clustering and assembling by the method of the present invention, the progress of this processing can be displayed on the display 1802. After completing this processing, the result of the processing can be also displayed on the display 1802.

Next, a parameter setting interface, a progress displaying interface, a result displaying interface, and a main interface for calling the above described interfaces which are displayed by the display 1802, the keyboard 1803, and the pointing device 1804 will be described.

The number of fixed-length partial sequences K to be entered into the fixed-length partial sequence table 103 from each input sequence, an upper limit R of a distance of the fixed-length partial sequence from respective ends of the input sequence, positions of respective fixed-length partial sequences, an upper limit c of an expected value of the number of entries matching with a coincidental key which is found at the time of referring to the fixed-length partial sequence table 103 independent of a true overlap, a fixed-length partial sequence length s, and an upper limit F of a frequency of occurrence of the partial sequence in the fixed-length partial sequence table 103 are input through the parameter setting interface. On the other hand, the number of processed sequences during the clustering and assembling processes and a ratio thereof to the number of whole input sequences, the number of configured clusters, an average of the number of elements which clusters constructed so far have, the position of each cluster member sequence in the consensus sequence, an exact matching sequence obtained by reference to the fixed-length partial sequence table 103 at the time of assembling, and a length of the overlap at the time of assembling are displayed through the progress displaying interface. After completing the processing, information about the input sequence or the cluster specified by the user is displayed through the result displaying interface as is the case of during the processing.

An example of the whole user interface according to the present invention will now be described with reference to FIGS. 9, 10, 11 and 12.

Figure 9:
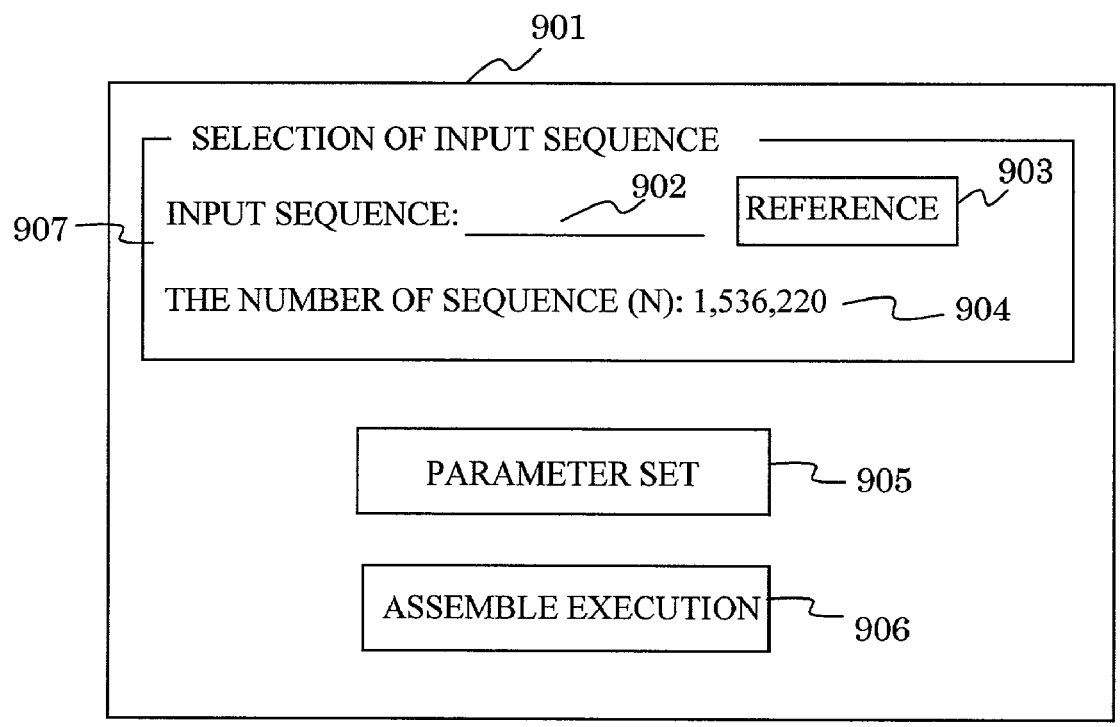
FIG. 9 shows an example of a main interface.

An example of the main interface will be described with reference to FIG. 9. This main interface 901 has an input sequence selecting part 907, a parameter setting button 905 allowing the parameter inputting interface to appear, and an assemble performing button 906 allowing a progress displaying interface to appear and performing the clustering and assembling.

The user firstly input a pass of a file, in which the input sequences are stored, into a file pass input area 902. In this example, a click on a reference button 903 with the pointing device 1804 allows a file dialog to appear. The file in which the input sequences are stored may alternatively be selected using the file dialog. When the file pass of the input sequences is input, the number of sequences N in the file is calculated and displayed on an area 904 for displaying the number of sequences.

After specifying an input sequence, a parameter setting interface is displayed by the click on the parameter setting button 905. An example of the parameter setting interface will be described later.

When the assemble performing button 906 is clicked, a progress displaying interface appears and the clustering and assembling processes starts. However, it is forbidden to click this button until input sequences are input. An example of the progress displaying interface will be described later. After the completion of the processing, the progress displaying interface is automatically closed, then a result displaying interface appears. An example of the result displaying interface will be described later.

Next, an example of the parameter setting interface will be described with reference to FIG. 10. The parameter setting interface 1001 shown in FIG. 10 has a fixed-length partial sequence position selecting part 1021, a fixed-length partial sequence length setting part 1022, and a fixed-length partial sequence key frequency upper limit inputting part 1023.

First, the user can input and specify the number K of fixed-length partial sequences to be extracted from each sequences at the time of clustering and assembling into an input area 1002 of the fixed-length partial sequence position selecting part 1021 by using the keyboard 1803 etc. Further, a parameter R which determines the upper limit of the distance between the fixed-length partial sequence and the 5'-end or the 3'-end of input sequences can be input to an input area 1003. The value R can also be specified by transversely moving a slider 1005 within a graphical user interface 1004. Boxes 1006 represent positions of extracting fixed-length partial sequences and have the width proportional to the length of the fixed-length partial sequences specified by reference numeral 1008 or 1009. The number of boxes 1006 displayed within this graphical user interface 1004 is equal to the value K specified in the input area 1002. The boxes 1006 can be freely moved along a line segment 1007 within R bases of each end by using the pointing device 1804 as long as the boxes do not overlap one another. When one of the boxes 1006 located in the vicinity of the head end of the line segment 1007 is intended to be R bases or more distant from the head end, the boxes 1006 forcibly moves to a position within R bases of a tail end of the line segment 1007. When one of the boxes 1006 located in the vicinity of the tail end of the line segment 1007 is intended to be R bases or more distant from the tail end, the boxes 1006 forcibly moves to a position within R bases of the head end of the line segment 1007.

The user can input and specify an upper limit c of an expected value of the number of entries which are found coincidentally despite lack of the true overlap at the time of referring the fixed-length partial sequence table 103 into the inputting and displaying area 1008 in the part 1022 for setting the fixed-length partial sequence length. When c is input, the length s of fixed-length partial sequences is automatically calculated as a minimum integer satisfying the expression (1), then the value s is displayed within the displaying area 1009. It is also possible to directly input and specify the fixed-length partial sequence length s into the area 1009 for inputting and displaying the length of fixed-length partial sequences. When s is input, a minimum value c satisfying the expression (1), that is, a minimum value c satisfying $NK/4^s \leq c$ is automatically calculated and displayed within the inputting and displaying area 1008.

In addition, an upper limit F of the key frequency in the fixed-length partial sequence table 103 is specified by the use of the area 1023 for inputting the upper limit of the fixed-length partial sequence key frequency.

First, the value F can be directly input to an inputting and displaying area 1011 as a numerical value. If the user chooses not to delete entries whose key frequencies are beyond the parameter F, a check box 1012 is checked. In addition, as means for specifying the value F, the value F can be set with reference to the actual frequency of occurrence of fixed-length partial sequences after producing the fixed-length partial sequence table 103. Within a graph displaying area 1013, a graph whose horizontal axis represents the frequency of occurrence and whose vertical axis represents the rank of the frequency of occurrence is displayed after constructing the fixed-length partial sequence table 103 based on the input sequences specified in the file pass input area 902. A scaling factor in a vertical direction can be changed by the slider 1017. On this graph, the value F can be set by moving the line segment 1014 representing F. On the other hand, a list is displayed within a displaying area 1015, in which a plurality of tupples of fixed-length partial sequences as keys and the frequencies of occurrence in the fixed-length partial sequence table 103 are aligned in descending order of their frequencies of occurrence. Also, the value F can be set even if the line segment 1016 representing the value F is moved within the displaying area 1015. When one of the three element, that is, the area 1011 for inputting and displaying the upper limit F, the line segments 1014 and 1016 representing F is operated to change the value F, representations on the remaining two elements are also changed in response to the renewal of the value F.

If the set of parameters specified with the interface described above is confirmed to be used for the clustering and assembling, a button 1018 is clicked. To abandon those parameters and restore them to those before displaying the parameter input interface, a button 1019 should be clicked.

Figure 11:
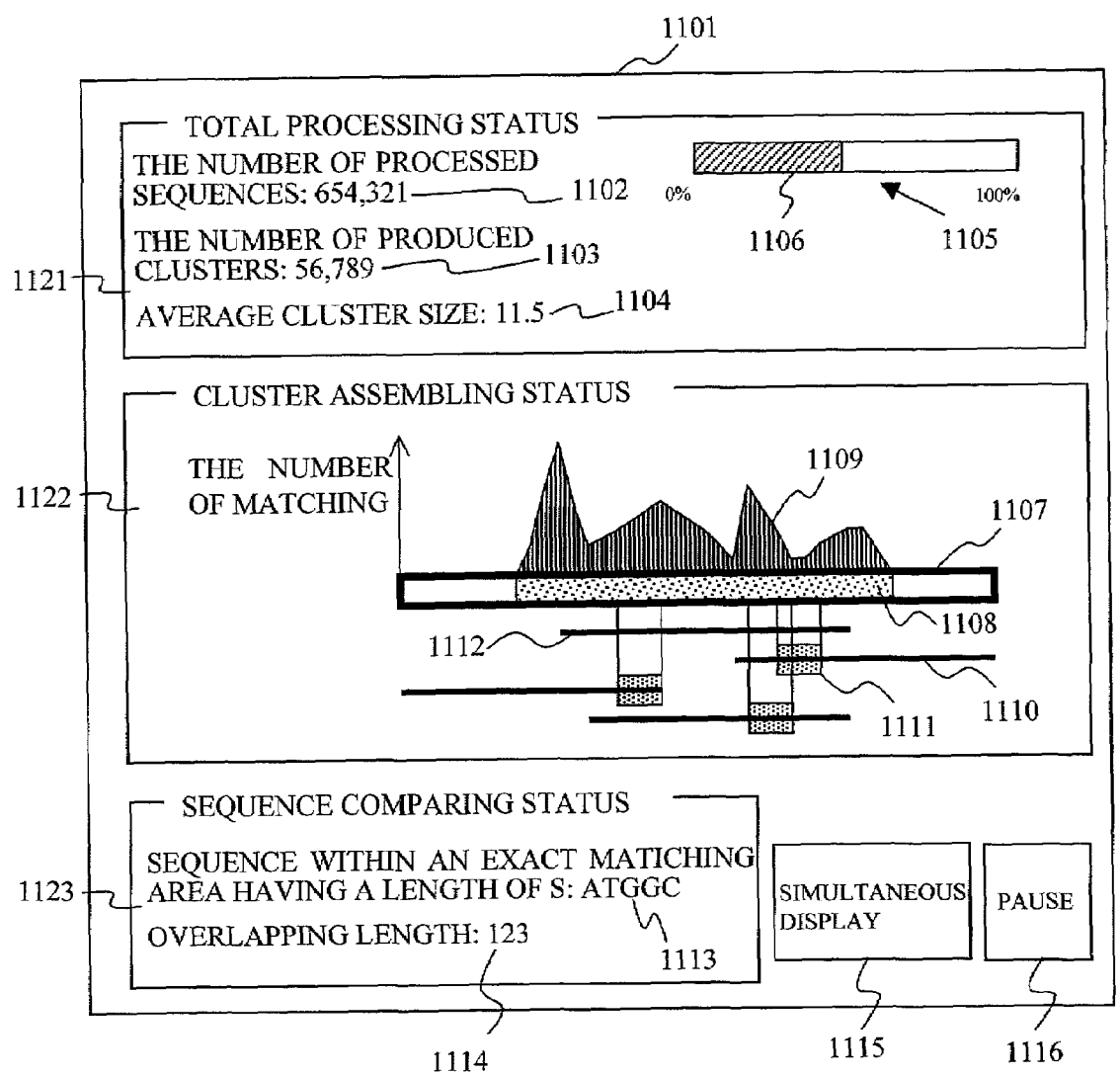
FIG. 11 shows an example of a progress displaying interface.

Next, an example of the progress displaying interface for displaying the processing progress of clustering and assembling will be described with reference to FIG. 11. The progress displaying interface 1101 of this example has a total processing status display 1121, a cluster assembling status display 1122, and a sequence comparing status display 1123.

On the total processing status display 1121, the number of sequences already added to any of the clusters is displayed within a displaying area 1102, the number of produced clusters is displayed within a displaying area 1103, and an average of the number of cluster elements is displayed within a displaying area 1104 during the processing. Within an area of a bar graph 1105, a part 1106 representing the number of processed sequences is displayed in the way to be easily discriminated from the other part in the bar graph, for example, using different color from the one of the remaining part.

An assembling status of each cluster is displayed on the cluster assembling status display 1122. The consensus sequence 104 is displayed as a horizontally oriented rectangle 1107. An area 1108 within the rectangle 1107 corresponding to an area which has been scanned by the fixed length window 105 is displayed in the way to be easily discriminated from the other area in the rectangle 1107. While the fixed length window 105 scans the consensus sequence 104, the number of detected exact matching found by using the partial string determined by the window 105 as a key is displayed after each time of referring to the fixed-length partial sequence table 103. An area in the consensus sequence 104 having an extremely high number of matching may suggest that the repeating sequences or functional domains exist.

An input sequence 502 assembled to the consensus sequence 104 is displayed as a horizontal line segment 1110. An area representing the exact matching having a length of s used for adding such an input sequence 502 to the cluster is displayed as an area 1111 in the way to be easily discriminated from the other area in the sequence. However, the sequence firstly added to the cluster is not added to the cluster based on the exact matching having a length of s, so that its display 1112 does not include the display 1111 showing the exact matching having a length of s.

In addition, when a new member is added to the cluster, the fixed-length partial sequence corresponding to the exact matching having a length of s is displayed within a displaying area 1113 of the sequence comparing status display 1123 and the overlapping length at the time of assembling is displayed within a displaying area 1114.

In order to prevent a decrease of speed with overhead of caused by displaying, displaying may be stopped or restarted after each time of clicking on a toggle button 1115 on which a sign "simultaneous display" is written. During pushing the button 1116 on which a sign "pause" is written, the display as well as the clustering and assembling processes can be temporarily suspended.

Figure 12:
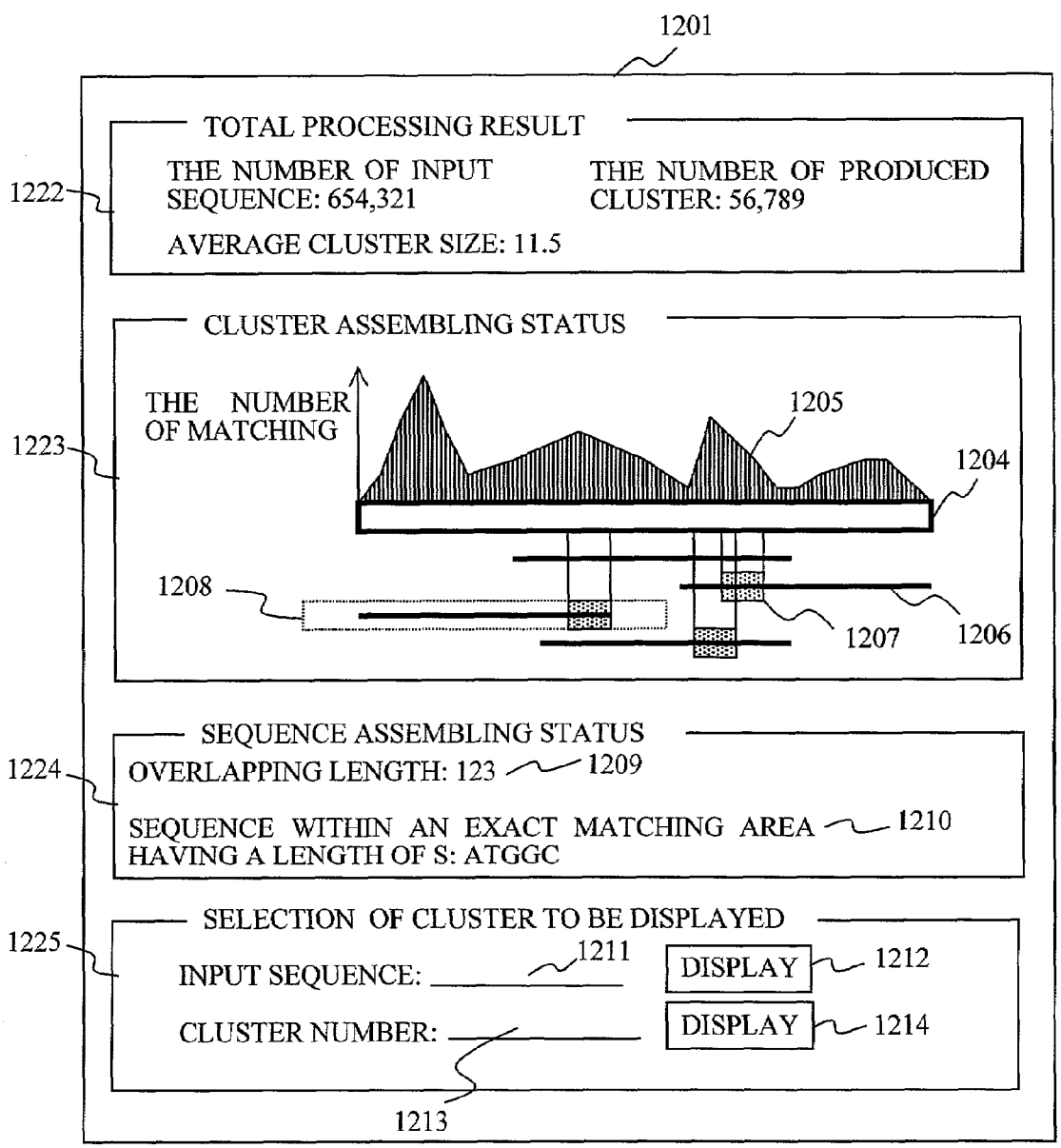
FIG. 12 shows an example of a result displaying interface.
Figure 13:
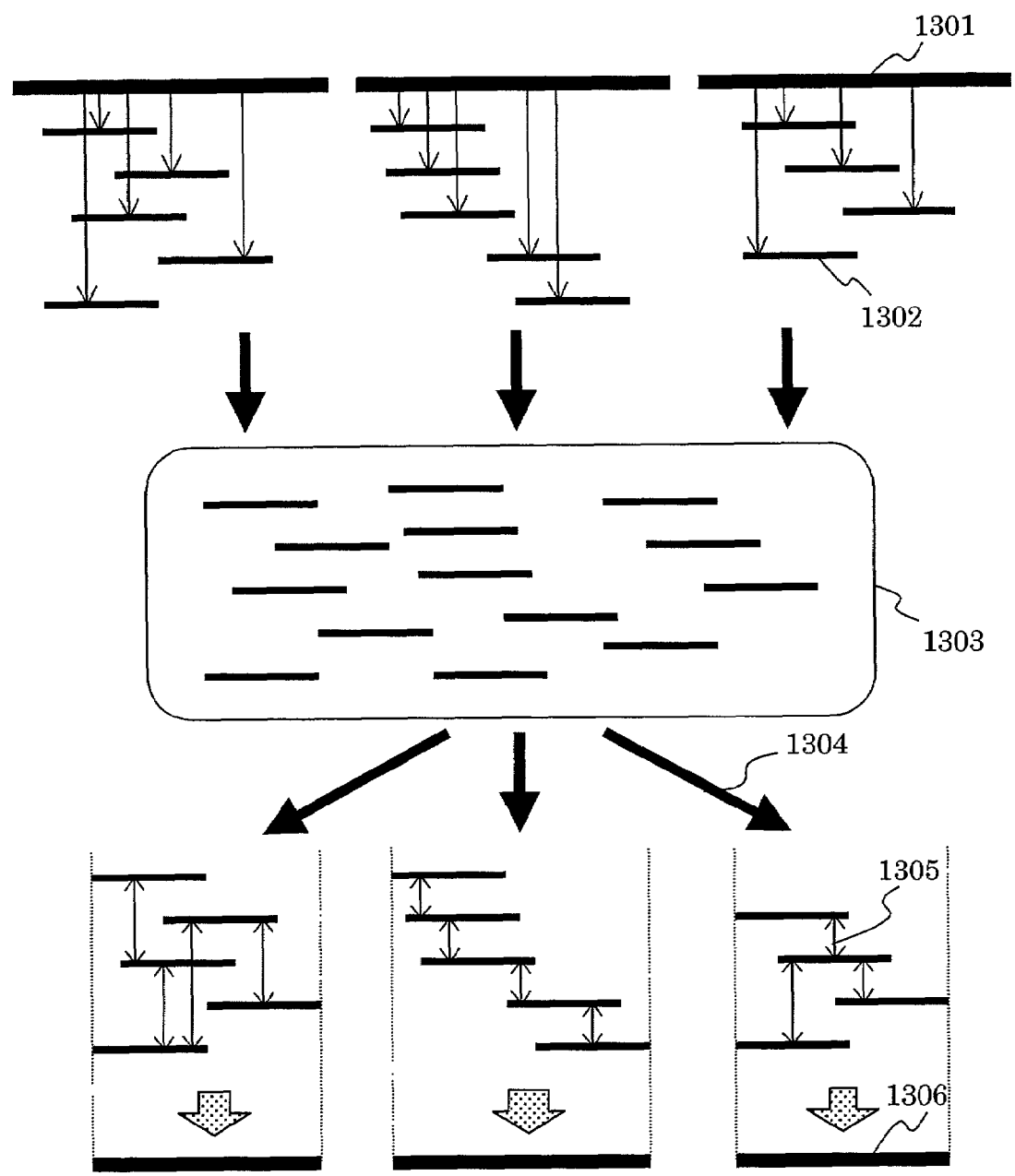
FIG. 13 schematically illustrates the clustering and assembling processes of EST derived from mRNA.

Next, an example of the result displaying interface for displaying results of clustering and assembling processes will be described with reference to FIG. 12. The result displaying interface 1201 shown in FIG. 12 has a displaying area 1222 for displaying the total processing result, a displaying area 1223 for displaying the cluster assembling status, a display area 1224 for displaying the sequence assembling status, and an area 1225 for selecting a cluster to be displayed.

The number of all input sequences, the number of produced clusters, and the average cluster size are displayed within the area 1222 for displaying the total processing result.

The displaying area 1223 for displaying the assembling status of each produced cluster will now be described. A display 1204 for showing the consensus sequence 104, a graph 1205 showing the frequency of exact matching having a length of s which has been found at the time of referring to the fixed-length partial sequence table 103, a line segment 1206 representing an input sequence 502 which is one of the cluster members, and an exact matching 1207 having a length of s used for adding the input sequence 502 to the cluster are respectively similar to the displays 1107, 1109, 1110 and 1111 of the progress displaying interface 1101. Although, in the progress displaying interface 1101, an exact matching sequence and an overlapping length about only the input sequence being processed are displayed within the displaying areas 1113 and 1114 as a sequence assembling status, in this result displaying interface 1201, it is possible to select any sequence in the cluster being displayed and to display an overlapping length 1209 and an exact matching sequence 1210 having a length of s. The sequence is displayed with emphasis by the use of a frame 1208 for example. The input sequence which is focused on can be changed to another sequence by clicking on the line segment 1206 with the pointing device 1804 or by the keyboard 1803.

The result displaying interface 1201 can also select a cluster to be displayed. After an input sequence name is input into an area 1211 of the input sequence name and a displaying button 1212 is clicked, an assembling status of the cluster including the input sequence is displayed. The input sequence specified by the user is displayed with emphasis by the frame 1208 for example, and the overlapping length and the exact matching sequence having a length of s about the input sequence are respectively displayed within the displaying areas 1209 and 1210. A cluster can also be specified and displayed in addition to the input sequence.

During the clustering and assembling processes, the cluster is displayed by numbering the output cluster in consecutive order, inputting the number into an inputting area 1213 and clicking on a displaying button 1214.

Actually, software for clustering and assembling the input sequence was implemented based on the method of the present invention for the purpose of testing it. This test implementation uses an array in stead of a two-way list for representing the consensus sequence, so that the asymptotic time complexity increases compared with the method of the present invention. Further, the test implementation of the fixed-length partial sequence table 103 uses a multimap class of the library STL of C++ language. According to this data structure, it is possible to perform the processing including element insertion, search, and deletion within a period of time proportional to a logarithm of the number of elements as is the case with the balanced-tree. This test implementation dose not include a graphical interface.

To perform the clustering and assembling processes, it is necessary to set the value s correctly. The expected value of the number of entries which are coincidentally found despite lack of true overlaps between input sequences is $NK/4^s$ or less provided that the sequence is random, and the computing time becomes shorter as the value s becomes greater. However, the value s is desirable to be as small as possible in order to minimize the possibility that errors are found in the sequences and the exact matching is not established. Under the condition that a computer word has 32-bits, it is necessary to use a fixed-length partial sequence having up to 16 bases if the sequence is represented by one computer word, on the other hand, the number of bases can be augmented up to 32 bases if a fixed-length partial sequence is represented by two computer words.

In order to determine an optimum value s, the time required for clustering and assembling was measured with the values N, K and s changed. The sequence data of interest was produced as follows in order to simulate the clustering and assembling of ESTs obtained from mRNAs. That is, one hundred thousand random sequences were prepared, the number of sequences being said to be the same as that of protein in human body and each of the sequences having a length of 2000 bases which was almost the same as the length of general mRNAs. Then sequences having a length of 500 bases which was the same as the length of ESTs were randomly extracted and created. A computer having a CPU clock frequency of 1.7 GHz and a main memory capacity of 1 GB was used. The results are shown in Table 1. Table 1 consists of the time required for clustering and assembling, an increasing rate of the processing time when the value s is decreased (a value obtained by dividing the processing time required when a length of the fixed-length partial sequence is s+1 by the processing time required when the length is s), and an expected value $NK/4^s$ of the number of entries coincidentally found at the time of referring to the fixed-length partial sequence table 103 independent of true overlaps between input sequence.

TABLE 1

| Time required for clustering and assembling processes (sec.) | | | | | | | |
|---|---|---|---|---|---|---|---|
| N | K | 20 | 19 | 18 | 17 | 16 | 15 |
| | | Length of fixed-length partial sequence (s) | | | | | |
| 65536 | 2 | 142 | 127 | 125 | 123 | 122 | 122 |
| 65536 | 8 | 156 | 154 | 150 | 151 | 149 | 150 |

TABLE 1-continued

Time required for clustering and assembling processes (sec.)

| | | | | | | | |
|---|---|---|---|---|---|---|---|
| 262144 | 2 | 526 | 478 | 474 | 469 | 466 | 466 |
| 262144 | 8 | 581 | 579 | 570 | 566 | 570 | 578 |
| 1048576 | 2 | 1537 | 1542 | 1526 | 1511 | 1513 | 1553 |

Increasing rate of processing time when fixed length partial character string length is decreased

| | | | | | | | |
|---|---|---|---|---|---|---|---|
| 65536 | 2 | — | 0.8943 | 0.9842 | 0.984 | 0.9918 | 1 |
| 65536 | 8 | — | 0.9871 | 0.974 | 1.0066 | 0.9867 | 0.9932 |
| 262144 | 2 | — | 0.9087 | 0.9916 | 0.9894 | 0.9936 | 0.9978 |
| 262144 | 8 | — | 0.9965 | 0.9844 | 0.9929 | 1.007 | 0.9877 |
| 1048576 | 2 | — | 1.0032 | 0.9896 | 0.9901 | 1.0013 | 1.0026 |

Expected value of coincidental matching of fixed length partial character string ($NK/4^s$)

| | | | | | | | |
|---|---|---|---|---|---|---|---|
| 65536 | 2 | 0 | 0 | 0 | 0.00001 | 0.00003 | 0.00012 |
| 65536 | 8 | 0 | 0 | 0.00001 | 0.00003 | 0.00012 | 0.00049 |
| 262144 | 2 | 0 | 0 | 0.00001 | 0.00003 | 0.00012 | 0.00049 |
| 262144 | 8 | 0 | 0.00001 | 0.00003 | 0.00012 | 0.00049 | 0.00195 |
| 1048576 | 2 | 0 | 0.00001 | 0.00003 | 0.00012 | 0.00049 | 0.00195 |

| N | K | 14 | 13 | 12 | 11 | 10 | 9 |
|---|---|---|---|---|---|---|---|

Length of fixed-length partial sequence (s)

| | | | | | | | |
|---|---|---|---|---|---|---|---|
| 65536 | 2 | 122 | 123 | 126 | 142 | 201 | 454 |
| 65536 | 8 | 150 | 153 | 166 | 222 | 450 | 1542 |
| 262144 | 2 | 466 | 481 | 535 | 753 | 1733 | 9297 |
| 262144 | 8 | 578 | 622 | 810 | 1575 | 5484 | — |
| 1048576 | 2 | 1553 | 1694 | 2293 | 5633 | — | — |

Increasing rate of processing time when fixed length partial character string length is decreased

| | | | | | | | |
|---|---|---|---|---|---|---|---|
| 65536 | 2 | 1 | 1.0081 | 1.0243 | 1.1269 | 1.4154 | 2.2587 |
| 65536 | 8 | 1.0135 | 1.02 | 1.0849 | 1.3373 | 2.027 | 3.4266 |
| 262144 | 2 | 1.0021 | 1.0321 | 1.1122 | 1.4074 | 1.3014 | 5.3646 |
| 262144 | 8 | 1.0266 | 1.0761 | 1.3022 | 1.9444 | 3.4819 | — |
| 1048576 | 2 | 1.0237 | 1.0907 | 1.3536 | 2.4566 | — | — |

Expected value of coincidental matching of fixed length partial character string ($NK/4^s$)

| | | | | | | | |
|---|---|---|---|---|---|---|---|
| 65536 | 2 | 0.00049 | 0.00195 | 0.00781 | 0.03125 | 0.125 | 0.5 |
| 65536 | 8 | 0.00195 | 0.00781 | 0.03125 | 0.125 | 0.5 | 2 |
| 262144 | 2 | 0.00195 | 0.00781 | 0.03125 | 0.125 | 0.5 | 2 |
| 262144 | 8 | 0.00781 | 0.03125 | 0.125 | 0.5 | 2 | 8 |
| 1048576 | 2 | 0.00781 | 0.03125 | 0.125 | 0.5 | 2 | 8 |

The first table shows that the computing time hardly changes when the value s is large, but the computing time sharply increases when the value s becomes smaller beyond a certain degree. For example, under the condition of N=65536 and K=2, a computing time required for a case of s=9 becomes two times longer than that required for a case of s=10. To shorten the computing time, it is desirable to set the value s within a range where the processing time does not sharply increase. Table 1 shows that it is necessary to set the value s at 10 or more at the minimum in order to suppress an increase of the computing time within a range of two times, when treating the data about the number of sequences which have been treated in this experiment. Considering Table 1 in more detail, it is found that the increasing rate of the computing time when $NK/4^s \leq 0.125$ is 1.5 or less. Thus, it is also found that providing c=0.125 and taking the value s so as to satisfy the expression (1) lead to savings in the computing time.

We have attempted to perform the clustering of nucleic acid sequences derived from mRNAs by the use of the above described software. The data used were sequence data disclosed in a database managed by the U.S. public institutions and the number of all sequences was 1,536,220 and the number of all bases was 656,663,661. A computer having a CPU clock frequency of 450 MHz and a main memory capacity of 4 GB was used. The fixed-length partial sequence length s which was given by the value c=0.125 and the expression (1) was 13. Further, the values K, R and F were as follows; K=2, R=13 (a partial sequence having a length of s=13 distant from a head end and from a tail end is entered into the fixed-length partial sequence table), and F=1.

It took 172 minutes and 57 seconds to complete the clustering and assembling processes. The number of obtained clusters was 732,166.

Although a software employing a method from the above described Huang, X. and Madan, A., Genome Research, 9:868–877, 1999 has been developed, it is impossible to simultaneously process one million sequenced because of the limitations of the number of input sequences. On the other hand, a method from Altschul, S. F. et al., Nucleic Acid Research, 25:3389–3402,1997 does not comprise the whole of clustering and assembling processes, but it is possible to perform an overlap search among sequences, which is a part of the clustering and assembling processing. However, it is predicted that a workstation having a CPU clock frequency of 450 MHz requires about 9 seconds for searching for every sequence which overlaps one sequence and that it takes about 160 days to search all overlaps potentially existing among 1,536,220 sequences.

The method of the present invention has been demonstrated to be effective because the above described software whose asymptotic time complexity is worse than that of the method of the present invention has successfully performed the clustering and assembling of the sequence data comprised of 1,536,220 sequences in such a short period of time as 172 minutes and 57 seconds.

According to another aspect of the present invention, following devices are provided.

(1) A device for assembling nucleic acid base sequences comprising:

input means for inputting parameters associated with fixed base length of partial sequences which are set in the head end and tail end region of each input nucleic acid base sequence;

means for entering identification information about each of a plurality of input nucleic acid base sequences and fixed-length partial sequences extracted from the nucleic acid base sequences based on the parameters input by said input means into a table, both of which are associated with each other;

means for searching for a nucleic acid base sequence which has a partial sequence matching with a part of a consensus sequence with reference to said table;

determination means for comparing the nucleic acid base sequence searched in said step with said consensus sequence and determining whether the both sequences can be assembled or not; and means for assembling said consensus sequence and said searched nucleic acid base sequence so as to reconstruct a consensus sequence if said determination means determines that the both sequences can be assembled.

(2) The device for assembling nucleic acid base sequences according to item (1) wherein said input means has a display for graphically displaying a position of said fixed base length of partial sequence in the input nucleic acid base sequence relative to a terminal of the sequence so that a position of a fixed-length partial sequence specified by a user can be immediately reflected on the display.

(3) The device for assembling nucleic acid base sequences according to item (1) wherein said input means inputs a number of fixed-length partial sequences to be extracted for one input nucleic acid base sequence and a number of bases in said fixed base length of partial sequence.

(4) The device for assembling nucleic acid base sequences according to item (1) wherein said input means specifies a length of the fixed base length of partial sequence to be entered into said table, based on an expected value of a number of coincidental matching detected at the time of referencing the table.

(5) The device for assembling nucleic acid base sequences according to any one of item (1) comprising a display for displaying graphics and/or numerical values representing a frequency of occurrence of each of said fixed-length partial sequences entered into said table.

(6) The device for assembling nucleic acid base sequences according to item (5) comprising means for specifying an upper limit of said frequency of occurrence and means for deleting an entry whose frequency of occurrence is beyond the upper limit specified from said table.

(7) The device for assembling nucleic acid base sequences according to item (1) comprising means for displaying each input nucleic acid base sequence assembled to said consensus sequence together with a position of the fixed-length partial sequence in said input nucleic acid base sequence matching with a part of said consensus sequence.

According to the present invention, it becomes possible to perform a clustering and assembling processes within $O(D(M+\log N))$-time, if D is the number of all bases in all input sequences, N is the number of all input sequences, and M is the length of the longest input sequence, so that the clustering of a massive amount of sequence data over 1.5 million sequences can be performed in several hours and graphical user interfaces are provided.

The invention claimed is:

1. A method for assembling nucleic acid base sequences comprising the steps of:

providing a plurality of nucleic acid base sequences;

moving an alignment window of a fixed base length along a first nucleic acid base sequence of the plurality of nucleic acid base sequences to define a first fixed-length sequence and simultaneously searching for a second nucleic acid base sequence having a terminal region matching exactly with the window of fixed base length;

determining whether the second nucleic acid base sequence and the first nucleic acid base sequence can be assembled or not by comparing a sequence adjacent to the aligned window of said first nucleic acid base sequence with a sequence adjacent to the aligned window of said second nucleic acid base sequence; and assembling said first nucleic acid base sequence and said second nucleic acid base sequence if the sequences adjacent to the aligned windows are similar.

2. A method for assembling nucleic acid base sequences according to claim 1, wherein the nucleic acid base sequence assembled in said assembling step is used as a reconstructed first nucleic acid base sequence to repeatedly carry out said moving, determining, and assembling steps.

3. A method for assembling nucleic acid sequences comprising the steps of:

providing a plurality of nucleic acid base sequences;

entering identification information of each of the plurality of nucleic acid base sequences and the respective fixed base length sequence located in a terminal region of each of the nucleic acid base sequences into a table;

constructing a first consensus sequence based on a first nucleic acid base sequence of the plurality of nucleic acid base sequences;

searching the table for a second nucleic acid base sequence among remaining ones of the plurality of nucleic acid base sequences which shares a fixed length sequence;

determining if the first nucleic acid base sequence and the second nucleic acid base sequence can be assembled by comparing the consensus and the second sequence where they are aligned at the exactly matching fixed length sequence; and if similar assembling said consensus sequence and second nucleic acid base sequences to reconstruct a new consensus sequence to repeatedly carry out the searching and determination steps.

4. The method for assembling nucleic acid base sequences according to claim 3, wherein a sequence whose base length is the longest among the plurality of nucleic acid base sequences is selected as said first nucleic acid base sequence.

5. A method for assembling nucleic acid base sequences comprising:
- a first step of sorting a plurality of nucleic acid base sequences in descending order of sequence lengths;
- a second step of entering, into a table, identification information of each of the plurality of nucleic acid base sequences and a respective pair of fixed base length partial sequences located in a terminal region thereof;
- a third step of selecting one of the nucleic acid base sequences whose sequence length is the longest among the plurality of nucleic acid base sequences as a first consensus sequence;
- a fourth step of moving a fixed base length alignment window along said first consensus sequence to define a first fixed-length partial sequence and simultaneously searching for a second nucleic acid base sequence among remaining ones of the plurality of partial nucleic acid base sequences which has an exact match with the fixed base length alignment window;
- a fifth step of determining if the first sequence and the second sequence can be assembled by comparing the consensus sequence and the second sequence where they are aligned at the exactly matching fixed-length partial sequence;
- a sixth step of assembling the consensus and second partial sequences to reconstruct a new consensus sequence,
- wherein the fourth step to the sixth step are repeated until said fixed base length alignment window completes the scanning throughout said reconstructed consensus sequence, and said third step to said sixth step are repeated until all of the plurality of nucleic acid base sequences are selected in the third or fourth step and compared in the fifth step.

6. The method for assembling nucleic acid base sequences according to claim 3, further comprising a step of picking up more than two of said fixed-length partial sequences to be entered into said table for each of the plurality of nucleic acid base sequences.

7. The method for assembling nucleic acid base sequences according to claim 3, further comprising the step of designating a range of the terminal region of said first nucleic acid base sequence from which said fixed base length partial sequences to be entered into said table is extracted.

8. The method for assembling nucleic acid base sequences according to claim 3, wherein the base length of said fixed base length partial sequences to be entered into said table is between 10 bases to 32 bases.

9. The method for assembling nucleic acid base sequences according to claim 3, further comprising the steps of:
- specifying an upper limit c as an expected number of entries retrieved from said table of a fixed base length partial sequence located in different nucleic acid base sequences or different positions in the plurality of nucleic acid base, and
- specifying a length s of fixed base length sequences to be entered into said table as an integer satisfying the following expression (1)

$$s \geq \frac{1}{2} \log \frac{KN}{c} \qquad (1)$$

where N is the number of said plurality of nucleic acid base sequences and K is the number of the fixed base length sequences selected from each of the plurality of nucleic acid base sequences.

10. The method for assembling nucleic acid base sequences according to claim 3, wherein each of said fixed base length sequences is represented by a fixed number of computing words which are independent of the length of the fixed-length partial sequences.

11. The method for assembling nucleic acid base sequences according to claim 3, wherein every entry which corresponds to a partial sequence having a frequency of occurrence beyond a parameter given by a user is deleted from said table.

12. The method of claim 1, wherein a greedy algorithm is used to compare the similarity between the sequence adjacent to the aligned window of said first partial nucleic acid base sequence with a sequence adjacent to the aligned window of said second partial nucleic acid base sequence.

13. The method of claim 3, wherein a greedy algorithm is used to compare the similarity between the sequences adjacent to the sections of the first and second nucleic acid base sequences aligned with said consensus sequence.

14. The method of claim 5, wherein a greedy algorithm is used to compare the similarity between the sequences adjacent to the sections of the first and second partial sequences aligned with said alignment window.

* * * * *